(12) United States Patent
Villahermosa Jaen et al.

(10) Patent No.: US 10,023,904 B2
(45) Date of Patent: Jul. 17, 2018

(54) METHOD FOR DETECTION OF KRAS MUTATIONS

(71) Applicant: GENOMICA S.A.U., Coslada, Madrid (ES)

(72) Inventors: Maria Luisa Villahermosa Jaen, Madrid (ES); Juan Moscoso del Prado, Madrid (ES)

(73) Assignee: Genomica S.A.U, Madrid (ES)

(*) Notice: Subject to any disclaimer, the term of this patent is extended or adjusted under 35 U.S.C. 154(b) by 536 days.

(21) Appl. No.: 14/367,770

(22) PCT Filed: Dec. 20, 2012

(86) PCT No.: PCT/EP2012/076350
§ 371 (c)(1),
(2) Date: Jun. 20, 2014

(87) PCT Pub. No.: WO2013/092839
PCT Pub. Date: Jun. 27, 2013

(65) Prior Publication Data
US 2016/0068893 A1    Mar. 10, 2016

(30) Foreign Application Priority Data
Dec. 23, 2011 (EP) .................................. 11382397

(51) Int. Cl.
| C12Q 1/68 | (2018.01) |
| C12Q 1/6827 | (2018.01) |
| C12Q 1/6858 | (2018.01) |
| C12Q 1/6886 | (2018.01) |
| G01N 33/574 | (2006.01) |

(52) U.S. Cl.
CPC ......... *C12Q 1/6827* (2013.01); *C12Q 1/6858* (2013.01); *C12Q 1/6886* (2013.01); C12Q 2600/156 (2013.01); G01N 2033/57465 (2013.01)

(58) Field of Classification Search
None
See application file for complete search history.

(56) References Cited

U.S. PATENT DOCUMENTS 7,560,542 B2 * 7/2009 Andersen ............. C07K 14/415
                                                536/23.6
9,512,473 B2 * 12/2016 Chen ................... C12Q 1/6858

FOREIGN PATENT DOCUMENTS

WO    WO 2006061994 A  *  6/2006   ............... C12Q 1/68

OTHER PUBLICATIONS

Bando et al. (JJCO, 2010, p. 2-6).*
Franklin et al. (J Molec Diagnostics, 2010, 12(1):p. 43-49).*
Lowe et al. (Nucleic Acids Research, 1990, 18(7):1757-1761).*
International Preliminary Report on Patentability in International Application No. PCT/EP2012/076350, entitled: "Method for Detection of KRAS Mutations," 10 pages, dated Jun. 24, 2014.

* cited by examiner

*Primary Examiner* — Stephanie K Mummert
(74) *Attorney, Agent, or Firm* — Hamilton, Brook, Smith & Reynolds, P.C.

(57) ABSTRACT

The present invention is based on a detection method of the 9 KRAS mutations Gly12Ser, Gly12Arg, Gly12Cys, Gly12Asp, Gly12Ala, Gly12Val, Gly13Asp, Gln61His and Gln61Leu, in a sample susceptible of containing one or more of such mutations, based on amplification of the sample with the primers of the present invention. Further, the present invention relates to (i) a kit which comprises, amongst its components, reagents for ARMS amplification including one or more of the primers of the present invention; (ii) the primers themselves; and (iii) use of the method, kit and primers of above, for the diagnosis/prognosis of a pathological condition in a patient, particularly, of cancer.

17 Claims, 14 Drawing Sheets

FIG. 1 a)

5' GGTGGAGTATTTGATAGTGTATTAACCTTATGTGTGACATGTTCTAATATAGTCA
CATTTTCATTATTTTTATTATAAGGCCTGCTGAAAATGACTGAATATAAACTTGTGG
TAGTTGGAGCT GGTGG CGTAGGCAAGAGTGCCTTGACGATACAGCTAATTCAGAATC
ATTTTGTGGACGAATATGATCCAACAATAGAGGTAAATCTTGTTTTAATATGCATAT
TACTGGTGCAGGACC 3' b)

Gly12Ser: AGTGG

Gly12Arg: CGTGG

Gly12Cys: TGTGG

Gly12Asp: GATGG

Gly12Ala: GCTGG

Gly12Val: GTTGG

Gly13Asp: GGTGA

FIG. 2A

| SEQ ID N° | Description | Sequence |
|---|---|---|
| 1 | 3'sequence of ARMS primer for amplification of KRAS mutation Gly12Ser, the sequence being target-specific | ctgaatataaacttgtggtagttggcgcta |
| 2 | 3'sequence of ARMS primer for amplification of KRAS mutation Gly12Arg, the sequence being target-specific | cgtcaaggcactcttgcctacgacacg |
| 3 | 3'sequence of ARMS primer for amplification of KRAS mutation Gly12Cys, the sequence being target-specific | ctgaatataaacttgtggtagttggagatt |
| 4 | 3'sequence of ARMS primer for amplification of KRAS mutation Gly12Asp, the sequence being target-specific | ctgaatataaacttgtggtagttggagccga |
| 5 | 3'sequence of ARMS primer for amplification of KRAS mutation Gly12Ala, the sequence being target-specific | ctgaatataaacttgtggtagttgcagatgc |
| 6 | 3'sequence of ARMS primer for amplification of KRAS mutation Gly12Val, the sequence being target-specific | cgtcaaggcactcttgcctacggcaa |

FIG. 2B

| 7 | 3'sequence of ARMS primer for amplification of KRAS mutation Gly13Asp, the sequence being target-specific | ctgaatataaacttgtggtagttggagctgggga |
|---|---|---|
| 8 | 3'sequence of ARMS primer for amplification of KRAS mutation Gln61His, the sequence being target-specific | tggtccctcattgcactgtactccaca |
| 9 | 3'sequence of ARMS primer for amplification of KRAS mutation Gln61Leu, the sequence being target-specific | gatattctcgacacagcagttct |
| 10 | ARMS primer for amplification of KRAS mutation Gly12Ser | aaggataattaattaatctgaatataaacttgtggtagttggcgcta |
| 11 | ARMS primer for amplification of KRAS mutation Gly12Arg | aatattgaggctgcagccgtcaaggcactcttgcctacgacacg |
| 12 | ARMS primer for amplification of KRAS mutation Gly12Cys | ggctagctagccgcggtagctgaatataaacttgtggtagttggagatt |
| 13 | ARMS primer for amplification of KRAS mutation Gly12Asp | cggtatttgggcaacctgctgaatataaacttgtggtagttggagccga |
| 14 | ARMS primer for amplification of KRAS mutation Gly12Ala | gaatccatgtgatgacttgctgaatataaacttgtggtagttgcagatgc |
| 15 | ARMS primer for amplification of KRAS mutation Gly12Val | tcaggcggccaggatggagcgtcaaggcactcttgcctacggcaa |
| 16 | ARMS primer for amplification of KRAS mutation Gly13Asp | ccgagacgttcgacactgcctgaatataaacttgtggtagttggagctgggga |

FIG. 2C

| 17 | ARMS primer for amplification of KRAS mutation Gln61His | ttaggctctgaactcggcgttggtccctcattgcactgtactccaca |
|---|---|---|
| 18 | ARMS primer for amplification of KRAS mutation Gln61Leu | ggccacttaccgggatccagatattctcgacacagcagttct |
| 19 | Amplification primer to be used in combination with any of ARMS primers comprising SEQ ID N° 1, 4, 7, or ARMS primers consisting of SEQ ID N° 10, 13, 16 | ggtcctgcaccagtaatatgca |
| 20 | Amplification primer to be used in combination with any of ARMS primers comprising SEQ ID N° 3, 5, or ARMS primers consisting of SEQ ID N° 12, 14 | ggtcctgcaccagtaatatgca |
| 21 | Amplification primer to be used in combination with any of ARMS primers comprising SEQ ID N° 2, 6, or ARMS primers consisting of SEQ ID N° 11, 15 | ggtggagtatttgatagtgta |
| 22 | Amplification primer to be used in combination with any of ARMS primer comprising SEQ ID N° 8, or ARMS primer consisting of SEQ ID N° 17 | gtttctcccttctcaggattccta |

FIG. 2D

| 23 | Amplification primer to be used in combination with any of ARMS primer comprising SEQ ID N° 9, or ARMS primer consisting of SEQ ID N° 18 | gggatattacctacctcataaaca |
|---|---|---|
| 24 | 5' sequence of ARMS primer for amplification of KRAS mutation Gly12Ser, the sequence being non-target-specific. This sequence is also present in the detection probe of KRAS mutation Gly12Ser | aaggataattaattaat |
| 25 | 5' sequence of ARMS primer for amplification of KRAS mutation Gly12Arg, the sequence being non-target-specific. This sequence is also present in the detection probe of KRAS mutation Gly12Arg | aatattgaggctgcagc |
| 26 | 5' sequence of ARMS primer for amplification of KRAS mutation Gly12Cys, the sequence being non-target-specific. This sequence is also present in the detection probe of KRAS mutation Gly12Cys | ggctagctagccgcggtag |

FIG. 2E

| 27 | 5' sequence of ARMS primer for amplification of KRAS mutation Gly12Asp, the sequence being non-target-specific. This sequence is also present in the detection probe of KRAS mutation Gly12Asp | cggtatttgggcaacctg |
|---|---|---|
| 28 | 5' sequence of ARMS primer for amplification of KRAS mutation Gly12Ala, the sequence being non-target-specific. This sequence is also present in the detection probe of KRAS mutation Gly12Ala | gaatccatgtgatgacttg |
| 29 | 5' sequence of ARMS primer for amplification of KRAS mutation Gly12Val, the sequence being non-target-specific. This sequence is also present in the detection probe of KRAS mutation Gly12Val | tcaggcggccaggatggag |
| 30 | 5' sequence of ARMS primer for amplification of KRAS mutation Gly13Asp, the sequence being non-target-specific. This sequence is also present in the detection probe of KRAS mutation Gly13Asp | ccgagacgttcgacactgc |

FIG. 2F

| 31 | 5' sequence of ARMS primer for amplification of KRAS mutation Gln61His, the sequence being non-target-specific. This sequence is also present in the detection probe of KRAS mutation Gln61His | ttaggctctgaactcggcgt |
|---|---|---|
| 32 | 5' sequence of ARMS primer for amplification of KRAS mutation Gln61Leu, the sequence being non-target-specific. This sequence is also present in the detection probe of KRAS mutation Gln61Leu | ggccacttaccgggatcca |
| 33 | Probe for detection of ARMS amplification product of KRAS mutation Gly12Ser | gcttgccccggggaaggataattaattaat |
| 34 | Probe for detection of ARMS amplification product of KRAS mutation Gly12Ser | ccccggggaaggataattaattaat |
| 35 | Probe for detection of ARMS amplification product of KRAS mutation Gly12Arg | ttcgccgggttacccgggaatattgaggctgcagc |
| 36 | Probe for detection of ARMS amplification product of KRAS mutation Gly12Arg | cgggttacccgggaatattgaggctgcagc |
| 37 | Probe for detection of ARMS amplification product of KRAS mutation Gly12Cys | ggctagctagccgcggtagctgaat |

FIG. 2G

| 38 | Probe for detection of ARMS amplification product of KRAS mutation Gly12Cys | cgaggccttggccggctagctagccgcggtagctgaat |
| --- | --- | --- |
| 39 | Probe for detection of ARMS amplification product of KRAS mutation Gly12Cys | cgaggccttggccggctagctagccgcggtag |
| 40 | Probe for detection of ARMS amplification product of KRAS mutation Gly12Cys | ccttggccggctagctagccgcggtagctgaat |
| 41 | Probe for detection of ARMS amplification product of KRAS mutation Gly12Cys | ccttggccggctagctagccgcggtag |
| 42 | Probe for detection of ARMS amplification product of KRAS mutation Gly12Asp | gcttgccccggggcggtatttgggcaacctg |
| 43 | Probe for detection of ARMS amplification product of KRAS mutation Gly12Asp | ccccggggcggtatttgggcaacctg |
| 44 | Probe for detection of ARMS amplification product of KRAS mutation Gly12Ala | gaatccatgtgatgacttg |
| 45 | Probe for detection of ARMS amplification product of KRAS mutation Gly12Ala | gaatccatgtgatgacttgacttg |
| 46 | Probe for detection of ARMS amplification product of KRAS mutation Gly12Ala | cgggttacccgggagtctcgaatccatgtgatgacttg |

FIG. 2H

| 47 | Probe for detection of ARMS amplification product of KRAS mutation Gly12Ala | cgggttacccggggaatccatgtgatgacttg |
|---|---|---|
| 48 | Probe for detection of ARMS amplification product of KRAS mutation Gly12Val | tcaggcggccaggatggagctgaat |
| 49 | Probe for detection of ARMS amplification product of KRAS mutation Gly12Val | cgggttacccgggtcaggcggccaggatggag |
| 50 | Probe for detection of ARMS amplification product of KRAS mutation Gly13Asp | ccgagacgttcgacactgcctgaat |
| 51 | Probe for detection of ARMS amplification product of KRAS mutation Gln61His | cgggttacccgggttaggctctgaactcggcgt |
| 52 | Probe for detection of ARMS amplification product of KRAS mutation Gln61His | cgggttacccgggagtctcttaggctctgaactcggcgt |
| 53 | Probe for detection of ARMS amplification product of KRAS mutation Gln61Leu | cgggttacccgggggccacttaccgggatcca |
| 54 | Probe for detection of ARMS amplification product of KRAS mutation Gln61Leu | cgggttacccgggagtctcggccacttaccgggatcca |

FIG. 3

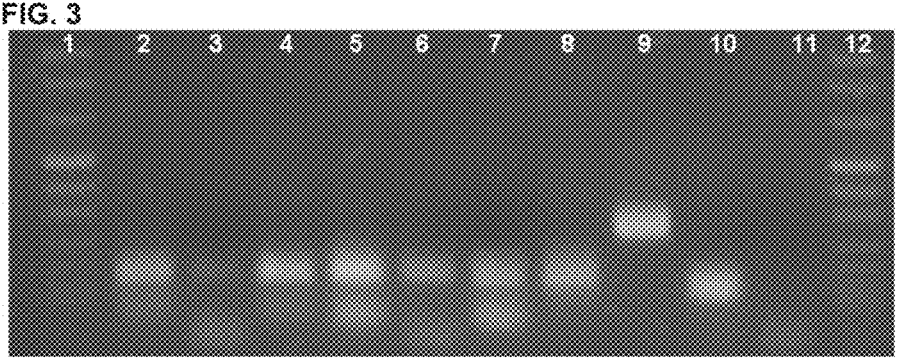

| Tube | Sample/ Clon | Result |
|---|---|---|
| 1 | Molecular weight marker | Well defined bands. Roche Molecular weight marker VIII |
| 2 | Sample G12S (Multiplex 1) | Mutation-specific band |
| 3 | Sample G12R (Multiplex 5) | Mutation-specific band |
| 4 | Sample G12D (Multiplex 1) | Mutation-specific band |
| 5 | Clon 10e5 G12C (Multiplex 4) | Mutation-specific band |
| 6 | Sample G12V (Multiplex 5) | Mutation-specific band |
| 7 | Clon 10e5 G12A (Multiplex 4) | Mutation-specific band |
| 8 | Sample G13D (Multiplex 1) | Mutation-specific band |
| 9 | Sample Q61L (Multiplex 5) | Mutation-specific band |
| 10 | Clon 10e4 Q61H (Multiplex 1) | Mutation-specific band |
| 11 | Negative Control (H2O) (Multiplex 5) | - |
| 12 | Molecular weight marker | Well defined bands. Roche Molecular weight marker VIII |

FIG. 4A
G12S
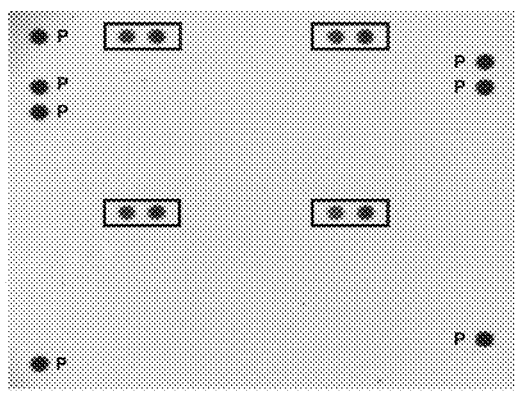
G12D
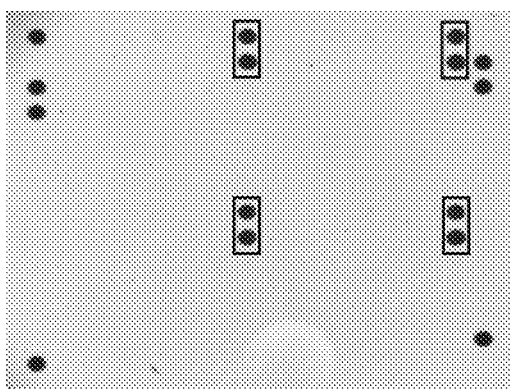
G13D
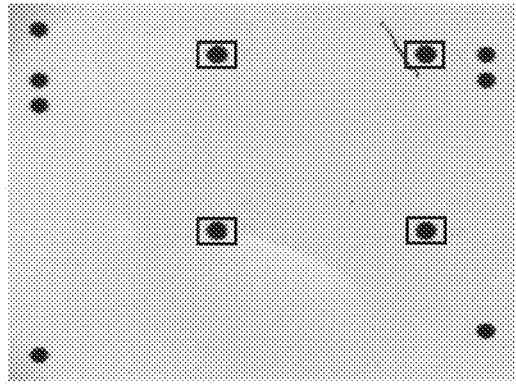
Q61H
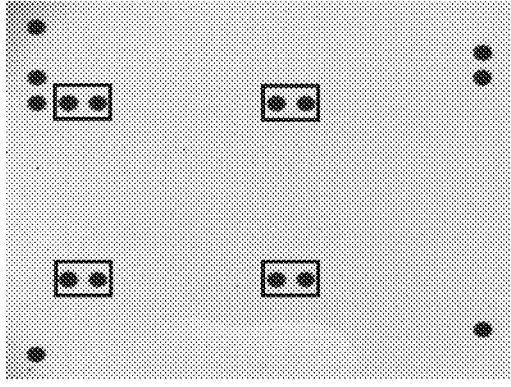

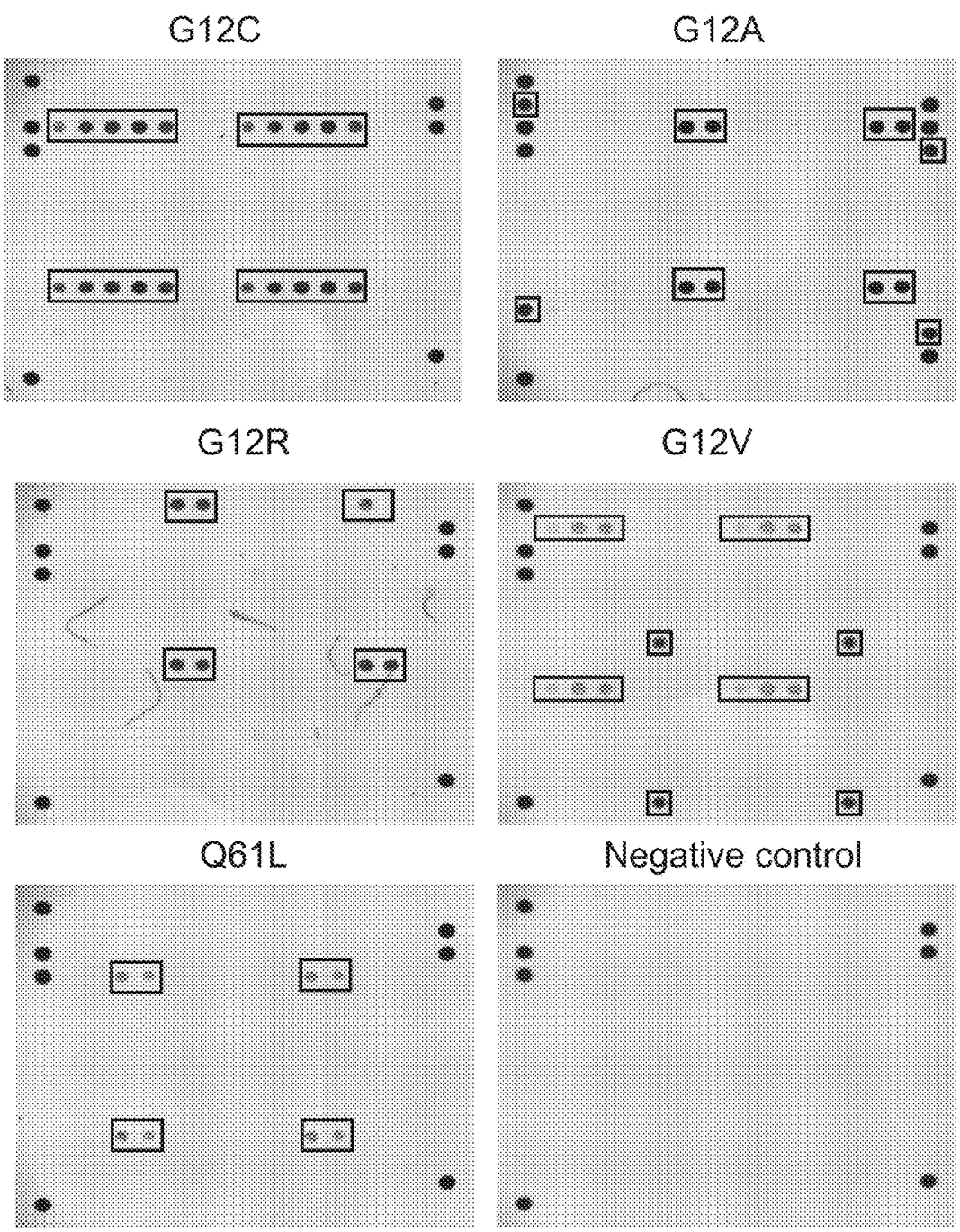

FIG. 5
a)
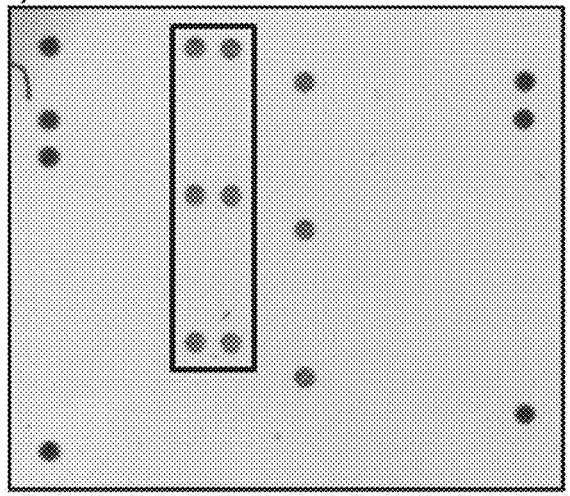
G12R KRAS (1000 copies)
b)
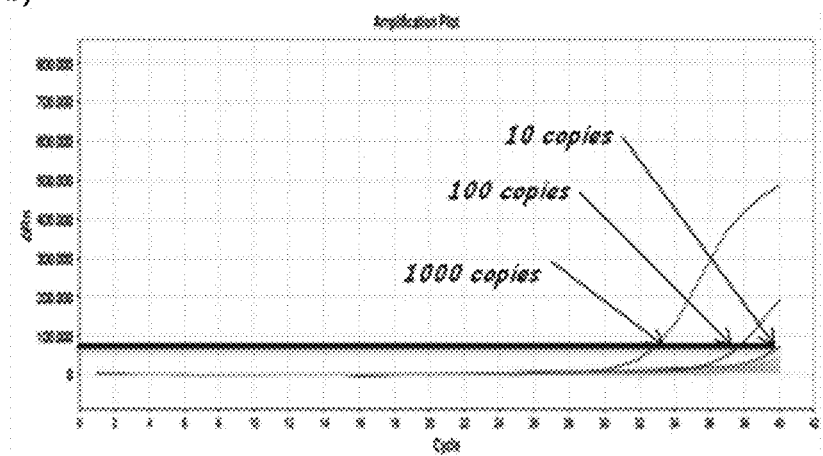
G12R KRAS
c)
| N° Copies | G12A | | G12C | | G12D | | G12R | | G12S | | G12V | | G13D | |
|---|---|---|---|---|---|---|---|---|---|---|---|---|---|---|
| | C | GS | C | GS | C | GS | C | GS | C | GS | C | GS | C | GS |
| $10^5$ | | | + | 29.5 | | | | | | | | | + | 28.7 |
| $10^4$ | | | + | 30.5 | | | | | | | | | + | 32.8 |
| $10^3$ | + | 31.2 | + | 33.6 | + | 37.2 | + | 31.8 | + | 37.3 | + | 32.2 | + | 36.4 |
| $10^2$ | | 35.3 | | 36.3 | | 38.4 | | 36.5 | | 38.6 | | 37.2 | | - |
| 10 | | 38.7 | | 38.5 | | | | 38.5 | | ~ | | ~ | | - |
G: Gold Standard (TheraScreen, Qiagen)
C: CMA, Kit of the present invention

METHOD FOR DETECTION OF KRAS MUTATIONS

RELATED APPLICATIONS

This application is the U.S. National Stage of International Application No. PCT/EP2012/076350, filed on Dec. 20, 2012, published in English, which claims the benefit of EP Application No. 11382397.5, filed on Dec. 23, 2011. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
 a) File name: 50771000000_SequenceListing.txt, created Jun. 16, 2017, 16 KB in size.

BACKGROUND OF THE INVENTION

KRAS is a Kirsten ras oncogene homolog from the mammalian ras gene family, which encodes a protein that is a member of the small GTPase superfamily. Mutations in the KRAS oncogene are frequently found in human pathologies, in particular cancer, wherein a single amino acid substitution in the KRAS protein may be responsible for an activating mutation. The mutated protein that results may be implicated in various malignancies, including lung adenocarcinoma, mucinous adenoma, ductal carcinoma of the pancreas and colorectal carcinoma.

Also, defects in KRAS can be a cause of acute myelogenous leukemia (AML), of juvenile myelomonocytic leukemia (JMML), of Noonan syndrome type 3 (NS3), and of cardiofaciocutaneous syndrome (CFC syndrome). Nearly 50% of colon cancers harbour activating mutations in KRAS, and also activating mutations in the KRAS oncogene are commonly associated with progression from a benign adenoma to an advanced/dysplastic adenocarcinoma. In addition, the presence of these mutations in KRAS correlates with a lack of response to certain anti-cancer therapies based on EGRF inhibition, in metastatic colorectal cancer patients. The evaluation of KRAS mutational status is thus often recommended to determine appropriate treatment.

Neoplasia-associated KRAS mutations frequently affect codons 12, 13 and 61. Mutations in codons 12 and 13 of KRAS are strong predictors of non-response to anti-EGFR antibodies in metastatic colorectal cancer (Shankaran et al., 2010, Oncologist 15, 157-167). Also, clinical studies indicate that codon 61 mutations are also associated with poor outcomes from anti-EGFR antibody therapy (De Roock et al., 2010, Lancet Oncol. 11, 753-762; Loupakis et al., 2009, Br. J. Cancer 101, 715-721). Codons 12 and 13 of the KRAS oncogene harbour 7 relevant mutations of KRAS: Gly12Ser (GGT/AGT), Gly12Arg (GGT/CGT), Gly12Cys (GGT/TGT), Gly12Asp (GGT/GAT), Gly12Ala (GGT/GCT), Gly12Val (GGT/GTT), and Gly13Asp (GGC/GAC). Also, codon 61 mutations, in particular, Gln61His (CAA>CAT) and Gln61Leu (CAA>CTA) are missense mutations, which abolish GTPase activity resulting in constitutively activated ras signaling.

There is a high demand for methods of detection of these 9 mutations of the KRAS gene. In particular, the state of the art often deals with the issue of detecting at least the 7 mutations corresponding to Gly12 and Gly13. FIG. 1a) displays the DNA fragment that contains the positions that give rise to the 7 KRAS mutations Gly12Ser, Gly12Arg, Gly12Cys, Gly12Asp, Gly12Ala, Gly12Val and Gly13Asp (the 5 nucleotides that determine the exact KRAS mutation are contained within the square). FIG. 1b) shows the exact nucleotide changes that give rise to each of the 7 KRAS mutations. A consequence of the fact that the 7 KRAS mutations all lay in close proximity within the KRAS gene sequence, and of the minimal sequence differences between the corresponding amplification products, is the non-specific hybridisation of any amplification product corresponding to one of the KRAS mutations, with probes complementary to the other KRAS mutations. Thus, hybridization to a probe of the DNA amplification product of any of the 7 KRAS mutations, is not specific, as the amplification fragment of other KRAS mutations may also non-specifically bind to the probe corresponding to the first one.

This drawback applies both to multiplex ARMS amplification, as well as to the individual ARMS amplification approach, wherein specific amplification products are obtained from each mutation in independent reaction vessels.

Another associated problem is that the KRAS mutations that may present as prognostic factors for tumour staging, metastasis, evolution, cellular heterogeneity, or allelic heterogeneity, are often to be found in samples in low abundance with respect to the wild type form. And, although many diagnostic methods are available for mutation detection, most cannot accurately detect low-abundance mutations. Sanger sequencing is the gold standard for KRAS mutation identification though it may only detect mutations in abundances above approximately 20%.

US2003/175750A1 (Barany Francis (US) et al.), discloses a method for detection of one or more nucleic acid differences, in particular, KRAS mutations, the method comprising a ligation step between two oligonucleotide probes ("Ligation Detection Reaction" or "LDR") as crucial step. According to the information displayed in US2003/175750A1, LDR would be the detection method for closely-clustered mutations such as those of KRAS, which are not amenable to detection by allele-specific PCR or hybridization.

Some other known detection methods used in the state of the art are based on PCR amplification of the DNA fragment of KRAS containing these mutations. The high sequence similarity between the DNA sequences of the KRAS mutations, prejudices specificity of detection of the amplification products. Subsequent detection of the PCR products in most methods of the state of the art thus takes place through some technical approaches such as DNA sequencing, visualisation in agarose gel, etc.

Two particular documents of the state of the art, WO 99/04037 and WO 2010/048691 disclose diagnostic methods for the detection of KRAS mutations, based on the amplification refractory mutation system (ARMS). ARMS is a method of detecting point mutations, based on the principle of allele-specific priming of PCR amplification (EP0332435; Newton et al., 1989, Nucleic Acid Research 17, 2503-2516). This system is based on a strategy wherein an oligonucleotide primer is designed so that it only functions as a primer for the PCR when it anneals to its specific target DNA sequence. The technique requires that the terminal 3'-nucleotide of the PCR primer be allele specific. This implies that the terminal 3'-nucleotide corresponds to that of the point mutation. Thus, the primer is designed in two forms: The "normal" form, which is refractory to PCR to "mutant" template DNA, and the "mutant" form, which is refractory to PCR on "normal" DNA.

In some instances, a single 3'-mismatched base does not completely prevent the non-specific extension of the oligonucleotide primer when having as target the DNA corresponding to another point mutation, and amplification proceeds.

In such cases, introduction of a deliberate mismatch near the 3' end of the allele-specific appropriate primer (at the second, third, or even fourth nucleotide from the 3' end of the primer) allows to enhance the specificity of the primer.

The ARMS technique involves that at least two PCRs may take place in one reaction mixture, each corresponding to amplification with one of the ARMS primers. Any ARMS primer further requires a second primer (that will be hereafter called amplification primer, and which is usually also called the common primer) to generate the allele-specific product. In addition, two or more control primers may be included in the reaction mixture in order to generate an unrelated product that indicates that the reaction is working correctly.

WO 99/04037 discloses detection of the 7 KRAS mutations Gly12Ser, Gly12Arg, Gly12Cys, Gly12Asp, Gly12Ala, Gly12Val and Gly13Asp present in a sample, based on ARMS amplification with the ARMS primers 1 to 7 displayed in Table 2 of WO 99/04037. Further to WO 99/04037, Yamada et al., 2005, Int. J. Cancer 113, 1015-1021, makes use of individual PCR amplification reactions, specific for each mutant allele, for detecting KRAS mutations in tumour and normal colorectal mucosa samples. Visualization of the amplification products is carried out after agarose gel electrophoresis and ethidium bromide staining. Simultaneous detection of ARMS products corresponding to different KRAS mutations, through hybridization with detection probes, for instance, would not be possible, the reason being the non-specific binding of the ARMS products of certain KRAS mutations to the probes of different KRAS mutations, due to sequence similarity.

WO 2010/048691 discloses a method of detection of KRAS mutations also based in ARMS amplification, but wherein the ARMS primers display a 3' fragment of 19 to 21 nucleotides (nt), complementary to the target sequence of the KRAS mutation to be detected, and a different non-specific 5' sequence that is used for detection. Thermal cycling conditions that are used for DNA amplification comprise a "hybridization temperature" of 54° C. and, usually, 50 PCR cycles are necessary for sensitive amplification. The 5' non-specific sequence is then used for detection of the amplification products. Detection of 50%, 25% or 5% mutant in wt background was tested with this method, detection of 5% mutant present in a wt background being the best sensitivity data achieved, but not for all KRAS mutations.

A drawback of this method is that some specificity problems arise, as it can be observed in data corresponding to Q61R, in Tables 8 and 9 of the patent application. Basically, not only the KRAS mutation present in the sample, but also other KRAS mutations, not present therein, are detected upon amplification with the ARMS primers of WO 2010/048691.

It would therefore be highly desirable to provide for an alternative method of detection of KRAS mutations present in a sample, that would allow specific detection of such mutations, while maintaining or enhancing the sensitivity values of the methods of the state of the art, in particular, of WO 2010/048691. The method should thus allow detection of KRAS mutations present within the sample in a 5% percentage or lower, in a wt background.

The invention described herein is aimed at providing a robust and reliable method for detecting KRAS mutations, and thus at mitigating the shortcomings in the prior art.

SUMMARY OF THE INVENTION

The problem to be solved by the present invention is the provision of an alternative method to those of the state of the art, for detection of any one of the 9 KRAS mutations Gly12Ser, Gly12Arg, Gly12Cys, Gly12Asp, Gly12Ala, Gly12Val, Gly13Asp, Gln61 His and Gln61Leu present in a sample, wherein the drawbacks of lack of specificity of the methods of the state of the art would be overcome. The method described herein allows to specifically detect any of above-mentioned KRAS mutations present in a sample, while providing equal or higher sensitivity values than the methods of the state of the art.

The solution, which is used in the different methods and aspects of the invention described herein, is based on ARMS (amplification refractory mutation system, method for detecting point mutations based on the principle of allele-specific priming of PCR amplification) amplification of one or more of the 9 KRAS mutations Gly12Ser, Gly12Arg, Gly12Cys, Gly12Asp, Gly12Ala, Gly12Val, Gly13Asp, Gln61 His and Gln61 Leu present in a sample, with one or more ARMS primers of the group of SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, as primers of KRAS mutations Gly12Ser, Gly12Arg, Gly12Cys, Gly12Asp, Gly12Ala, Gly12Val, Gly13Asp, Gln61 His and Gln61Leu, respectively.

The ARMS primers of the present invention comprise a 3' target specific sequence selected from SEQ ID No 1, SEQ ID No 2, SEQ ID No 3, SEQ ID No 4, SEQ ID No 5, SEQ ID No 6, SEQ ID No 7, SEQ ID No 8, and SEQ ID No 9, respectively, each primer further comprising a different non-target specific 5' tag sequence of from 17 to 30 nucleotides, which is used for detection.

The respective specific ARMS primers for the 9 KRAS mutations Gly12Ser, Gly12Arg, Gly12Cys, Gly12Asp, Gly12Ala, Gly12Val, Gly13Asp, Gln61His and Gln61 Leu used in the different aspects of the invention, can be depicted as indicated in Table 1.

TABLE 1

SEQ ID NO: 1
5' tag1-CTGAATATAAACTTGTGGTAGTTGGCGCTA 3',

SEQ ID NO: 2
5' tag2-CGTCAAGGCACTCTTGCCTACGACACG 3',

SEQ ID NO: 3
5' tag3-CTGAATATAAACTTGTGGTAGTTGGAGATT 3',

SEQ ID NO: 4
5' tag4-CTGAATATAAACTTGTGGTAGTTGGAGCCGA 3',

SEQ ID NO: 5
5' tag5-CTGAATATAAACTTGTGGTAGTTGCAGATGC 3',

SEQ ID NO: 6
5' tag6-CGTCAAGGCACTCTTGCCTACGGCAA 3'

TABLE 1-continued

```
                                    SEQ ID NO: 7
5' tag7-CTGAATATAAACTTGTGGTAGTTGGAGCTGGGGA 3'

SEQ ID NO: 8
5' tag8-TGGTCCCTCATTGCACTGTACTCCACA 3'

SEQ ID NO: 9
5' tag9-GATATTCTCGACACAGCAGTTCT 3'.
```

Tag1, tag2, tag3, tag4, tag5, tag6, tag7, tag8 and tag9, located in the 5' position of the ARMS primers, represent the non-target specific nucleotide sequences, all being different from each other. Further, the 3' target-specific sequences are designed according to the ARMS amplification method.

Throughout the present patent specification these mutation-specific amplification primers designed in accordance with the ARMS amplification method, will be named "ARMS primers". Additionally, the primer or primers that combine with the ARMS primers for target DNA amplification, also called the common primers, will be named "amplification primers". The latter can be either forward or reverse, depending on whether the ARMS primers are reverse or forward, respectively.

The difference between the ARMS primers of the present invention and those of WO 2010/048691 is the length of the 3' target-specific fragment, complementary to the target sequence of the KRAS mutation to be detected. Thus, the ARMS primers of the present invention display 3' target-specific fragments of the following lengths: 34 nt (SEQ ID No 16), 31 nt (SEQ ID No 13; SEQ ID No 14), 30 nt (SEQ ID No 10; SEQ ID No 12), 27 nt (SEQ ID No 11; SEQ ID No 17), 26 nt (SEQ ID No 15), and 23 nt (SEQ ID No 18). Differently, all the 3' target-specific fragments of the ARMS primers of WO 2010/048691 are 19 to 21 nt-long, most of them being 20 nt-long.

Amplification with the ARMS primers of the present invention allow the use of thermal cycling conditions that comprise a "hybridization temperature" in the range of 60 to 64° C., preferably, of 62° C., which is higher than the 54° C. "hybridization temperature" of WO 2010/048691. Amplification at this higher amplification temperature enhances specificity of detection, as each primer will only hybridize to its target sequence. Differently, at lower hybridization temperatures non-specific binding of the primers to different mutations is unavoidable. Specificity data with the primers of the present invention are all comprised between 98.5 and 100%.

Yet another difference that is achieved thanks to the ARMS primers of the present invention relates to the number of cycles of the PCR amplification reaction. Thus, the number of cycles of the PCR amplification reaction according to the method of the present invention is preferably of 40-42 cycles. Differently, the most usual amplification conditions of WO 2010/048691 comprise 50 PCR cycles. A higher number of PCR cycles is requested when adequate sensitivity values cannot be achieved with a lower number of cycles, which is the case of the closest state of the art. Amplification with the ARMS primers of the present invention, however, provides better sensitivity values than those of WO 2010/048691, and these are achieved with a lower number of PCR cycles. A consequence of this reduction in the number of PCR cycles with the primers of the present invention is an enhancement of specificity, while at a higher number of cycles non-specific amplification of other KRAS mutations cannot be avoided. Further, use of the primers of the present invention provides the present detection method with sensitivity values wherein 1% KRAS mutant can be detected in a wt background (See Example 2 below). This sensitivity value is better than that of WO 2010/048691, wherein the optimal sensitivity value achieved is detection of 5% KRAS mutant in a wt background.

The method of the present invention allows Multiplex ARMS amplification with two or more ARMS primers of the present invention.

A further advantage of the method of the present invention is that it allows detection of KRAS mutations that are present in the sample in a low percentage (1% mutant in a wt background).

In one of the aspects of the invention, the invention relates to a method for detecting one or more KRAS mutations selected from Gly12Ser, Gly12Arg, Gly12Cys, Gly12Asp, Gly12Ala, Gly12Val, Gly13Asp, Gln61 His and Gln61Leu in a test sample comprising nucleic acid, wherein said method comprises subjecting the sample to amplification with a mixture comprising one or more ARMS primers selected from SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, respectively, the amplification mixture further comprising one or more amplification primers.

Further to the ARMS and amplification primers, the amplification mixture also comprises additional reagents for nucleic acid amplification, such as a DNA polymerase and dNTPs.

Preferably, the hybridization temperature that is used in the PCR amplification reaction is of from about 60° C. to about 64° C., preferably of about 62° C. most preferably 62° C. Also, preferred thermal cycling conditions of the amplification reaction are selected from:

| NUMBER OF CYCLES | TEMPERATURE | TIME |
| --- | --- | --- |
| 1 cycle | 95° C. | 15' |
| ≥40 cycles (preferably 40-42 cycles) | 94° C. | 15-30" (preferably 15") |
| | 60-64° C. (preferably 62° C.) | 45-90" (preferably 60") |
| 1 cycle | 62-72° C. (preferably 72° C.) | 6-12' (preferably 10') |
| 1 cycle | 4° C. | Forever |

Preferably, the method of the present invention comprises contacting the one or more amplification products obtained, with one or more probes, each probe specifically hybridising to the region in the product corresponding to the 5' tag sequence of the corresponding ARMS primer.

Another aspect of the present invention relates to a kit for detecting one or more KRAS mutations selected from Gly12Ser, Gly12Arg, Gly12Cys, Gly12Asp, Gly12Ala, Gly12Val, Gly13Asp, Gln61His and Gln61Leu in a test sample comprising nucleic acid, wherein said kit comprises one or more mixtures of reagents for nucleic acid amplification (amplification mixtures), each mixture comprising:
  one or more ARMS primers selected from SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, respectively, and
  one or more amplification primers,
the kit further comprising a microarray wherein one or more probes that specifically bind to the ARMS products of one or more of the KRAS mutations Gly12Ser, Gly12Arg, Gly12Cys, Gly12Asp, Gly12Ala, Gly12Val, Gly13Asp, Gln61 His and Gln61 Leu, are immobilised, each probe specifically hybridising to the region in the corresponding ARMS product complementary to the 5' tag sequence of the corresponding ARMS primer.

A third aspect of the present invention corresponds to an ARMS primer selected from the group comprising SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18.

Yet another aspect of the present invention corresponds to the use of the method, the kit, or the ARMS primers as described herein, for diagnosis and/or prognosis of a pathologic condition in a patient. Preferably, the pathologic condition is cancer. Most preferably, the cancer is colorectal cancer. Another aspect relates to a method for detecting/diagnosing cancer in a patient comprising a detection or amplification method as described herein. Additionally, a further aspect of the present invention corresponds to prediction of response of a patient to therapy with anti-EGFR antibodies, through performance of the methods and kit of the present invention.

As already stated, the ARMS primers used in the method of the invention comprise in the 3' end, a target specific sequence which is capable of hybridising to the target nucleic acid in an allele specific way. This 3' target-specific sequence may be of from 23 to 34 nt-long. This primer also comprises a 5' sequence which is not target specific and thus not complementary to the target nucleic acid. This sequence is a tag sequence which is useful in detecting the amplification product through subsequent hybridisation with a probe specifically designed to hybridise to the region of the amplification product complementary to the tag sequence. This allows specific detection of the amplification product amplified by the methods described herein.

The method of the present invention thus comprises contacting a test sample from a patient comprising nucleic acids with one or more diagnostic ARMS primers of the present invention, in the presence of one or more amplification primers, appropriate nucleotide triphosphates and an agent for polymerisation and under the appropriate conditions, such that each diagnostic primer is extended only when its corresponding KRAS mutation is present in the sample; and detecting the presence or absence of a KRAS mutation by reference to the presence or absence of a diagnostic primer extension product. The agent for polymerisation and the appropriate conditions can be selected by the skilled person.

One or more of the ARMS primers selected from SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18 can be used alone or in combination with one or more of the other ARMS primers. In one embodiment, 1, 2, 3, 4, 5, 6, 7, 8 or 9 of these primers are used.

In particular, the method of the present invention allows to specifically detect any amplification product, obtained from any of the 9 KRAS mutations Gly12Ser, Gly12Arg, Gly12Cys, Gly12Asp, Gly12Ala, Gly12Val, Gly13Asp, Gln61His and Gln61Leu present in a sample, by hybridization of such product with one or more probes that specifically hybridize to it in the region corresponding to the tag provided by the specific primer. In particular, according to the methods of the invention, the probes may be comprised in a microarray. Preferably, the probes may be immobilized on a solid support.

Specially preferred primers combinations are primer mixtures comprising:
One or more ARMS primers selected from SEQ ID No 10, SEQ ID No 13, SEQ ID No 16 and SEQ ID No 17 (Components of Amplification Mixture 1);
One or more ARMS primers selected from SEQ ID No 12, SEQ ID No 14 and SEQ ID No 18 (Components of Amplification Mixture 2);
One or more ARMS primers selected from SEQ ID No 11 and SEQ ID No 15 (Components of Amplification Mixture 3);
One or more ARMS primers selected from SEQ ID No 12 and SEQ ID No 14 (Components of Amplification Mixture 4); and
One or more ARMS primers selected from SEQ ID No 11 and SEQ ID No 15 (Components of Amplification Mixture 5).

As amplification primer, any possible primer of between 17 and 35 nucleotides, that upon combination with one or more of the ARMS primers of above, results in amplification products of 1,000 bp or shorter, might be used for amplification. The amplification primer can be either forward or reverse, depending on whether the corresponding ARMS primer is reverse or forward, respectively.

Preferably, an amplification primer comprising SEQ ID No 19, and most preferably, a primer consisting of sequence SEQ ID No 19, is used in combination with one or more of the ARMS primers of SEQ ID No 10, SEQ ID No 13 and SEQ ID No 16.

Also, preferably, an amplification primer comprising SEQ ID No 20, and most preferably, a primer consisting of sequence SEQ ID No 20, is used in combination with one or two of the ARMS primers of SEQ ID No 12 and SEQ ID No 14.

Also, preferably, an amplification primer comprising SEQ ID No 21, and most preferably, a primer consisting of sequence SEQ ID No 21, is used in combination with one or two of the ARMS primers of SEQ ID No 11 and SEQ ID No 15.

Also, an amplification primer comprising SEQ ID No 22, and most preferably, a primer consisting of sequence SEQ ID No 22, is used in combination with the ARMS primer of SEQ ID No 17.

In addition, an amplification primer comprising SEQ ID No 23, and most preferably, a primer consisting of sequence SEQ ID No 23, is used in combination with the ARMS primer of SEQ ID No 18.

The detection probes of the present invention specifically hybridise to the region in the product complementary to the 5' tag sequence of the corresponding primer. Preferably, the 5' tag may be selected from one of the following sequences SEQ ID No 24, SEQ ID No 25, SEQ ID No 26, SEQ ID No 27, SEQ ID No 28, SEQ ID No 29, SEQ ID No 30, SEQ ID No 31 and SEQ ID No 32.

The 5' tag sequences of the different primers, are all different from the others. This difference is what makes possible the specific binding of the different amplification products to their corresponding probes, for any probe specific for one of the amplification products must have a nucleotide sequence able to hybridise at least to the region in the product corresponding to the corresponding tag. Probes of the present invention thus preferably comprise a sequence selected from SEQ ID No 24, SEQ ID No 25, SEQ ID No 26, SEQ ID No 27, SEQ ID No 28, SEQ ID No 29, SEQ ID No 30, SEQ ID No 31, and SEQ ID No 32, and may contain additional nucleotides to those specific to the tag region.

Preferred probes of the present invention are probes of SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54 and SEQ ID No 55.

The probes according to this aspect of the invention may be immobilised on a solid support. The set of probes of the microarray and solid support may further comprise one or more control probes. Preferably, the kit of the present invention further comprises reagents for the visualization of the hybridisation between any amplification product and the microarray of probes.

BRIEF DESCRIPTION OF THE DRAWINGS

FIG. 1.

FIG. 1 a) displays a DNA fragment (SEQ ID No 55) that contains the nucleotide positions that give rise to the 7 KRAS mutations Gly12Ser, Gly12Arg, Gly12Cys, Gly12Asp, Gly12Aia, Gly12Val and Gly13Asp. The 5 nucleotides that determine the exact KRAS mutation, are those contained within the square.

FIG. 1 b) shows the exact nucleotide changes that correspond to each of the 7 KRAS mutations.

FIGS. 2A-2H.

Figure 6:
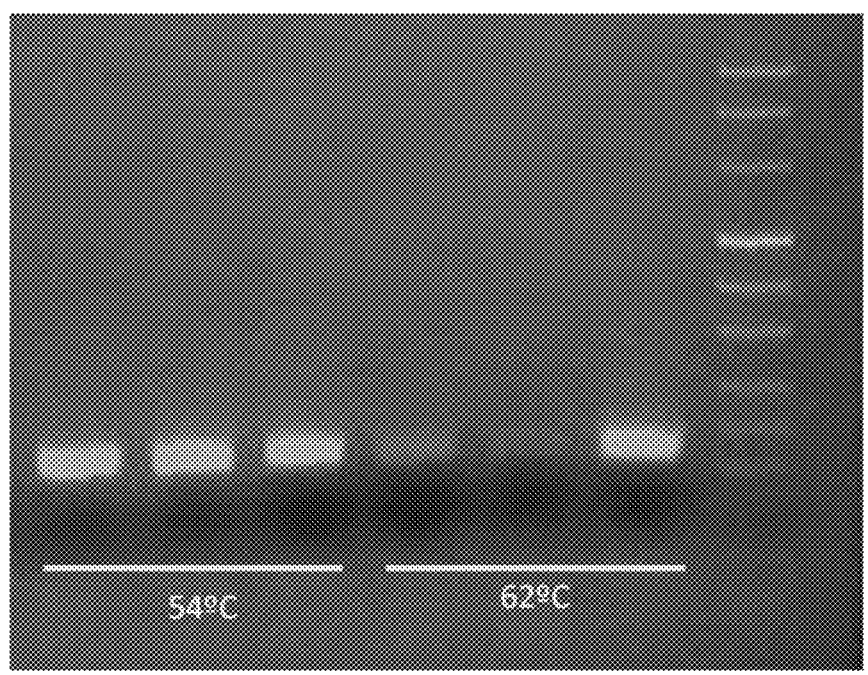

Nucleic acid sequences of SEQ ID No 1 to 54, and corresponding descriptions.

FIG. 3.

FIG. 3 displays visualization in an agarose gel, of the products of the Multiplex ARMS amplification carried out with the ARMS and amplification primers of the present invention, and the indicated samples/clones corresponding to the indicated different KRAS mutations.

Length of the amplification product corresponding to mutations:

KRAS Gly12 and Gly13: ~164 bp
KRAS Gln61 His: ~102 bp KRAS, and Gln61Leu: 240 bp Shorter additional bands which are observed are artefacts resulting from ARMS and amplification primers, but they nevertheless do not modify the final results obtained in the subsequent visualization step. It has also been confirmed that variations in the number of amplification cycles do not modify the results obtained.

FIGS. 4A and 4B.

FIGS. 4A and 4B display visualization of the hybridization with a microarray comprising the probes of the present invention, corresponding to the products that result from amplification with ARMS and amplification primers of the present invention, of the samples/clones indicated in Example 1 and FIG. 3.

The spots named "P" in the first of the images correspond to the Position Marker, and are present in all the microarrays in the same position. The spots corresponding to the specific binding, in the different microarrays, of the different ARMS amplification products with their specific probes, are contained within squares/rectangles.

FIG. 5.

FIG. 5 shows a comparison between results with the method of the present invention and those of a Gold Standard method (TheraScreen of Qiagen).

FIG. 5a) shows the result of detection with the kit of the present invention, CMA, of a sample comprising 1,000 copies of a G12R KRAS clone in 5 µl. The spots contained within the rectangle in the microarray correspond to the specific binding of the G12R KRAS ARMS amplification product with its specific probes; Remaining spots correspond to different controls;

FIG. 5b) displays a plot corresponding to detection of 10/100/ and 1,000 copies of a G12R KRAS clone in 5 µl with the Gold Standard kit TheraScreen of Qiagen.

FIG. 5c) is a Table with the different results obtained with the kits CMA and TheraScreen, for different dilutions of clones corresponding to the indicated KRAS mutations.

FIG. 6.

Result of amplification of KRAS Gly12Ser mutation, at two different hybridization temperatures, 54° C. and 62° C., according to example 4:

FIG. 6 shows the amplification products corresponding to KRAS mutation Gly12Ser at two different hybridization temperatures, 54° C. and 62° C., as visualized after agarose gel electrophoresis.

Lanes 1 and 4 correspond to amplification product of 1 ng of cell line NCI-H460 (Gly12Ser negative);
Lanes 2 and 5 correspond to amplification product of 1 ng of cell line HCT 116 (Gly12Ser negative);
Lanes 3 and 6 correspond to amplification product of cell line A549 (Gly12Ser positive);
Lane 7 corresponds to Roche's Molecular Weight Marker VIII.

DETAILED DESCRIPTION OF THE INVENTION

In the following passages, different aspects of the present invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

A first aspect of the present invention is a method for detecting one or more KRAS mutations selected from Gly12Ser, Gly12Arg, Gly12Cys, Gly12Asp, Gly12Ala, Gly12Val, Gly13Asp, Gln61His and Gln61Leu in a test sample comprising nucleic acid, wherein said method comprises subjecting the sample to amplification with a mixture comprising one or more ARMS primers selected from SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, respectively, the amplification mixture further comprising one or more amplification primers.

The method of the present invention may also preferably comprise detecting any amplification product, through hybridization of any such product with one or more specific probes, wherein the specific probe to any KRAS mutation specifically hybridizes with the product at least in the region corresponding to the 5' tag sequence tag1, tag2, tag3, tag4, tag5, tag6, tag7, tag8 or tag9 provided by the specific ARMS primer.

The methods of the present invention imply that, further to the ARMS and amplification primers, any additional components known by the skilled person to be necessary for nucleic acid amplification, in particular, for PCR amplification, may also be present within the amplification mixture. Thereby, a DNA polymerase and dNTPs, may also be present within the amplification mixture.

Preferably, the amplification product is transformed into single-stranded DNA prior to hybridization with the corresponding probe. Most preferably single-stranded DNA is obtained through denaturation of the amplification product, most preferably, through heat-denaturation. Preferably, the probe specifically hybridises to the region in the product complementary to the 5' tag sequence of the specific ARMS primer. Target-specific probes may be provided in a microarray.

A second aspect of the present invention corresponds to a kit for detecting one or more KRAS mutations selected from Gly12Ser, Gly12Arg, Gly12Cys, Gly12Asp, Gly12Ala, Gly12Val, Gly13Asp, Gln61His and Gln61Leu in a test sample comprising nucleic acid, wherein said kit comprises one or more mixtures of reagents for nucleic acid amplification, each mixture comprising:
   one or more ARMS primers selected from SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, respectively, and
   one or more amplification primers,
the kit further comprising a microarray wherein one or more probes that specifically bind to the ARMS products of one or more of the KRAS mutations Gly12Ser, Gly12Arg, Gly12Cys, Gly12Asp, Gly12Ala, Gly12Val, Gly13Asp, Gln61 His and Gln61 Leu, are immobilised, each probe specifically hybridising to the region in the corresponding ARMS product complementary to the 5' tag sequence of the corresponding ARMS primer.

As in the case of the methods of above, the kit of the present invention implies that, further to the ARMS primer or amplification primers, any additional components known by the skilled person to be necessary for nucleic acid amplification, in particular, for PCR amplification, such as a DNA polymerase and dNTPs, may also be present within the amplification mixture.

Definitions

Throughout the present disclosure, unless otherwise stated, the term "ARMS primers" refers to the KRAS mutation-specific amplification primers designed in accordance with the ARMS amplification method; and the term "amplification primers" refers to the primers that combine with the ARMS primers for target DNA amplification.

The ARMS primers used in the different aspects of the invention can be represented as displayed in Table 1 above. The fragments located in the 5' position of the primers, i.e.: tag1, tag2, tag3, tag4, tag5, tag6, tag7, tag8 and tag9 constitute the 5' tag sequence or "tag", there being no substantial homology between the tag sequences. By no substantial homology is meant less than 50% homology (i.e. two tag sequences do not share more than 50% of their nucleotides).

The ARMS primers of the present invention corresponding to KRAS mutations Gly12Ser, Gly12Arg, Gly12Cys, Gly12Asp, Gly12Ala, Gly12Val, Gly13Asp, Gln61His and Gln61Leu, are, respectively, as follows:

(SEQ ID No 10)
AAGGATAATTAATTAATCTGAATATAAACTTGTGGTAGTTGGCGCTA (SEQ ID No 11)
AATATTGAGGCTGCAGCCGTCAAGGCACTCTTGCCTACGACACG (SEQ ID No 12)
GGCTAGCTAGCCGCGGTAGCTGAATATAAACTTGTGGTAGTTGGAGATT (SEQ ID No 13)
CGGTATTTGGGCAACCTGCTGAATATAAACTTGTGGTAGTTGGAGCCGA (SEQ ID No 14)
GAATCCATGTGATGACTTGCTGAATATAAACTTGTGGTAGTTGCAGATGC (SEQ ID No 15)
TCAGGCGGCCAGGATGGAGCGTCAAGGCACTCTTGCCTACGGCAA (SEQ ID No 16)
CCGAGACGTTCGACACTGCCTGAATATAAACTTGTGGTAGTTGGAGCTGGGGA (SEQ ID No 17)
TTAGGCTCTGAACTCGGCGTTGGTCCCTCATTGCACIGTACTCCACA
and (SEQ ID No 18)
GGCCACTTACCGGGATCCAGATATTCTCGACACAGCAGTTCT, Nucleotides in bold correspond to the tag.

Respective 5' tags, thus, correspond to SEQ ID No 24, SEQ ID No 25, SEQ ID No 26, SEQ ID No 27, SEQ ID No 28, SEQ ID No 29, SEQ ID No 30, SEQ ID No 31, and SEQ ID No 32.

As amplification primer, any possible primer of between 17 and 35 nucleotides, that upon combination with one or more of the ARMS primers consisting of SEQ ID No 10, SEQ ID No 11, SEQ ID No 12, SEQ ID No 13, SEQ ID No 14, SEQ ID No 15, SEQ ID No 16, SEQ ID No 17, and SEQ ID No 18, results in amplification products of 1,000 bp or shorter, might be used for amplification. In a preferred embodiment, the amplification primer combined with one or more ARMS primers of above for amplification, produces amplification products of 500 bp or shorter, in another preferred embodiment, of around 200 bp, and in a most preferred embodiment, of between 200 bp and 100 bp. The amplification primer can be either forward or reverse, depending on whether the corresponding ARMS primer is reverse or forward, respectively.

Preferably, according to the different aspects of the invention, an amplification primer comprising SEQ ID No 19, and most preferably, a primer consisting of sequence SEQ ID No 19, is used in combination with one or more of the ARMS primers of SEQ ID No 10, SEQ ID No 13 and SEQ ID No 16.

Also, preferably, an amplification primer comprising SEQ ID No 20, and most preferably, a primer consisting of sequence SEQ ID No 20, is used in combination with one or two of the ARMS primers of SEQ ID No 12 and SEQ ID No 14.

Also, preferably, an amplification primer comprising SEQ ID No 21, and most preferably, a primer consisting of sequence SEQ ID No 21, is used in combination with one or two of the ARMS primers of SEQ ID No 11 and SEQ ID No 15.

Also, an amplification primer comprising SEQ ID No 22, and most preferably, a primer consisting of sequence SEQ ID No 22, is used in combination with the ARMS primer of SEQ ID No 17.

In addition, an amplification primer comprising SEQ ID No 23, and most preferably, a primer consisting of sequence SEQ ID No 23, is used in combination with the ARMS primer of SEQ ID NQ 18.

In a preferred aspect, any specific probe for detection of any of the KRAS mutations Gly12Ser, Gly12Arg, Gly12Cys, Gly12Asp, Gly12Ala, Gly12Val, Gly13Asp, Gln61 His and Gln61Leu according to the invention, has a length of from 17 to 39 nucleotides, the region which specifically hybridizes with the corresponding ARMS product in the region corresponding to tag1, tag2, tag3, tag4, tag5, tag6, tag7, tag8 or tag9 being of between 17 and 30 nucleotides. Each probe may also comprise additional nucleotides, either in the 5' and/or in the 3' end, up to the total length of from 17 to 39 nucleotides.

Preferably, the specific probes for detection of KRAS mutations Gly12Ser, Gly12Arg, Gly12Cys, Gly12Asp, Gly12Ala, Gly12Val, Gly13Asp, Gln61His and Gln61Leu, comprise the nucleotide sequences of SEQ ID No 24, SEQ ID No 25, SEQ ID No 26, SEQ ID No 27, SEQ ID No 28, SEQ ID No 29, SEQ ID No 30 and SEQ ID No 31 and SEQ ID No 32, respectively.

The most preferred probes for each of the KRAS mutations according to the different aspects of the invention are displayed in Table 2.

| KRAS mutation | Probe sequence | Probe Name | SEQ ID No |
|---|---|---|---|
| Gly12Ser | GCTTGCCCCGGGGAAGGATAATTAATTAAT | S-34 A7.2 | 33 |
| Gly12Ser | CCCCGGGGAAGGATAATTAATTAAT | S-34 A7.4 | 34 |
| Gly12Arg | TTCGCCGGGTTACCCGGGAATATTGAGGCTGCAGC | S-34 C13.2 | 35 |
| Gly12Arg | CGGGTTACCCGGGAATATTGAGGCTGCAGC | S-34 C13.4 | 36 |
| Gly12Cys | GGCTAGCTAGCCGCGGTAGCTGAAT | S-34 T18.5 | 37 |
| Gly12Cys | CGAGGCCTTGGCCGGCTAGCTAGCCGCGGTAGCTGAAT | S-34 T18.6 | 38 |
| Gly12Cys | CGAGGCCTTGGCCGGCTAGCTAGCCGCGGTAG | S-34 T18.7 | 39 |
| Gly12Cys | CCTTGGCCGGCTAGCTAGCCGCGGTAGCTGAAT | S-34 T18.8 | 40 |
| Gly12Cys | CCTTGGCCGGCTAGCTAGCCGCGGTAG | S-34 T18.9 | 41 |
| Gly12Asp | GCTTGCCCCGGGGCGGTATTTGGGCAACCTG | S-34 A7.6 | 42 |
| Gly12Asp | CCCCGGGGCGGTATTTGGGCAACCTG | S-34 A7.7 | 43 |
| Gly12Ala | GAATCCATGTGATGACTTG | S-35 C3 | 44 |
| Gly12Ala | GAATCCATGTGATGACTTGACTTG | S-35 C4 | 45 |
| Gly12Ala | CGGGTTACCCGGGAGTCTCGAATCCATGTGATGACTTG | S-35 C5 | 46 |
| Gly12Ala | CGGGTTACCCGGGAATCCATGTGATGACTTG | S-35 C6 | 47 |
| Gly12Val | TCAGGCGGCCAGGATGGAGCTGAAT | S-34 C13.5 | 48 |
| Gly12Val | CGGGTTACCCGGGTCAGGCGGCCAGGATGGAG | S-34 C13.7 | 49 |
| Gly13Asp | CCGAGACGTTCGACACTGCCTGAAT | S-38 A2 | 50 |
| Gln61His | CGGGTTACCCGGGTTAGGCTCTGAACTCGGCGT | S-61 H3 | 51 |
| Gln61His | CGGGTTACCCGGGAGTCTCTTAGGCTCTGAACTCGGCGT | S-61 H4 | 52 |
| Gln61Leu | CGGGTTACCCGGGGGCCACTTACCGGGATCCA | S-61 L1 | 53 |
| Gln61Leu | CGGGTTACCCGGGAGTCTCGGCCACTTACCGGGATCCA | S-61 L2 | 54 |

One or more different probes may be used for detecting each KRAS mutation. In particular, the probes are immobilized on a microarray. A microarray is a collection of microscopic oligonucleotide spots. A DNA microarray (also commonly known as gene chip, DNA chip, or biochip) is a collection of microscopic DNA spots attached to a solid surface. Probes are synthesized and then attached via surface engineering to a solid surface by a covalent bond to a chemical matrix (via epoxy-silane, amino-silane, lysine, polyacrylamide or others). Solid surfaces are known in the art and include microscopic beads as well as solid supports. In particular, the probes of the present invention may be immobilized on a solid support.

Thereby, further to the mixture for amplification, the kit of the present invention comprises a microarray wherein one or more probes that specifically hybridize to one or more of the products of KRAS mutations Gly12Ser, Gly12Arg, Gly12Cys, Gly12Asp, Gly12Ala, Gly12Val, Gly13Asp, Gln61His and Gln61Leu are immobilised.

For a better understanding of the present invention, the nucleotide sequences of SEQ ID No 1 to SEQ ID No 54 described herein, are displayed in FIGS. 2A-2H.

One or more controls may be included in the methods and kit of the present invention. Preferably, a pair of amplification primers corresponding to any constitutive and ubiquitous human gene known to the skilled person, may be included in the amplification mixture. Most preferably, amplification primers corresponding to β-actin gene are used. Amplification with such a pair of primers allows to confirm the correct extraction of the nucleic acid present in the test sample, and constitutes the "Endogenous control" or "Extraction control". Additionally, a DNA plasmid and a pair of primers with ability to amplify it, are preferably included in the amplification mixture, and constitute the "Amplification control" or "Internal control". Preferably, the microarray may comprise one or more control probes with ability to hybridize to corresponding control DNA sequences, in particular, to the products of the extraction and amplification controls.

Preferably, the kit of the present invention further comprises reagents for the visualization of the hybridisation between any amplification product and the microarray of probes.

A further aspect of the present invention corresponds to one or more ARMS primers selected from the group comprising SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18.

Yet another aspect of the present invention corresponds to the use of the method described herein, or of the kit described herein, or of the primers described herein, for diagnosis and/or prognosis of a pathological condition in a patient, in particular, of cancer, as well as for the prediction of response of a patient to therapy with anti-EGFR antibodies. In particular, if a KRAS mutation is present in the sample, then the patient is not likely to respond to anti-EGFR therapy. Thus, the invention also relates to an in vitro method for diagnosing a subject or assessing a subject for an appropriate chemotherapy, comprising:

(i) providing a tumor sample from the subject;
(ii) determining whether a KRAS mutation is present in the sample using the methods described herein.

In one embodiment, if a KRAS mutation is present in the sample, then a therapy comprising anti-EGFR is determined not to be appropriate.

In a preferred embodiment, types of test samples that can be processed by the present invention are swabs, paraffin-embedded biopsies, blood, sputum, colonic lavage, bronchial lavage, as well as saline, plasma, and cerebral spinal fluid, and any other body fluid, or tissue obtained from an individual. The individual is human.

The test sample may equally be a nucleic acid sequence corresponding to the sequence in the test sample. All or a part of the region in the sample nucleic acid may firstly be amplified using any convenient technique such as PCR before use in the method of the invention.

In another preferred embodiment, extraction of genetic material can be carried out both by automatic as well as by manual extraction techniques of the state of the art.

A specially preferred DNA extraction method from tissues and other samples, is QIAGEN's EZ1® DNA Tissue Kit. Also preferred is QIAGEN's product AllPrep® DNA/RNA FFPE, which is intended for simultaneous purification of genomic DNA and total RNA from formalin-fixed, paraffin-embedded tissue sections. Any other techniques and methods for manual or automatic processing of samples to extract DNA and other nucleic acids, the skilled person may be aware of, may be used within the present invention.

In a preferred embodiment of the present invention, the vessel wherein the method of the present invention takes place comprises, further to the one or more ARMS primers and the one or more amplification primers, other components for amplification of the DNA present in the sample. In particular, appropriate nucleotide triphosphates, such as dATP, dCTP, dGTP, dTTP, and a suitable enzyme for polymerisation are also included in the mixture of amplification reagents.

Any convenient enzyme for polymerisation may be used. In particular, any DNA polymerase with ability to discriminate between normal and mutant template sequences to any significant extent. Examples of convenient enzymes include thermostable enzymes which have no significant 3'-5'exonuclease activity, and with polymerization rates of around 10 nucleotides/second, thereby yielding amplification fragments of 600-1,000 bp in standard extension steps. Preferably QIAGEN's HotStarTaq DNA Polymerase may be used, which utilizes a chemically-mediated hot-start that, unlike antibody-mediated systems, leads to complete inactivation of the polymerase until the initial heat activation step. Any other enzyme with these characteristics known in the state of the art, may also be used. For instance, "Ampli Taq Gold" DNA polymerase of PE Applied Biosystems.

ARMS amplification of the different KRAS mutations of the present invention may be carried out either individually, or in a Multiplex amplification reaction of two or more of the KRAS mutations. In both cases, QIAGEN Multiplex PCR Kit is most preferably used for ARMS amplification, within the methods and kits of the present invention.

The method of the present invention can be carried out in one or more reaction vessels, each vessel comprising at least one ARMS primer of the present invention, and at least one amplification primer, together with other reagents for amplification.

Thermal cycling conditions that work well include the following ranges of temperatures and times:

| NUMBER OF CYCLES | TEMPERATURE | TIME |
|---|---|---|
| 1 cycle | 95° C. | 15' |
| ≥40 cycles (preferably 40-42 cycles) | 94° C. | 15-30" (preferably 15") |
|  | 60-64° C. (preferably 62° C.) | 45-90" (preferably 60") |
| 1 cycle | 62-72° C. (preferably 72° C.) | 6-12' (preferably 10') |
| 1 cycle | 4° C. | Forever |

The first temperature mentioned (i.e. 95° C.), can be named "activation temperature"; The second temperature mentioned (i.e. 94° C.), can be named "denaturation temperature";

The subsequent range of temperatures that is mentioned (i.e. about 60 to about 64° C., preferably, 62° C.), can be named "hybridization temperature", which is also the temperature at which extension of the PCR products takes place;

Yet the subsequent range of temperatures that is mentioned (i.e. about 62 to about 72° C., preferably, 72° C.), can be named "termination temperature"; Finally, the final 4° C. temperature that is mentioned, corresponds to a temperature wherein the PCR products are stable.

Thermal cycling conditions that have proven to work particularly well with samples are:

| NUMBER OF CYCLES | TEMPERATURE | TIME |
|---|---|---|
| 1 cycle | 95° C. | 15' |
| 40 cycles | 94° C. | 15" |
|  | 62° C. | 60" |
| 1 cycle | 72° C. | 10' |
| 1 cycle | 4° C. | Forever |

Any possible combination of the ARMS primers of the present invention can be used for Multiplex detection of one or more of the 9 KRAS mutations Gly12Ser, Gly12Arg, Gly12Cys, Gly12Asp, Gly12Ala, Gly12Val, Gly13Asp, Gln61His and Gln61Leu present in a sample.

Thus, the reaction vessel wherein the method of the present invention takes place, may comprise 1, 2, 3, 4, 5, 6, 7, 8 or 9 of the ARMS primers selected from the group comprising SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, as well as one or more amplification primers that might be combined with the ARMS primers of above for amplification of one or more of the 9 KRAS mutations Gly12Ser, Gly12Arg, Gly12Cys, Gly12Asp, Gly12Ala, Gly12Val, Gly13Asp, Gln61His and Gln61Leu present in a sample.

Additional primer pairs, preferably those corresponding to extraction and/or internal controls, may also be included in the amplification mixture according to the different aspects of the invention.

Some specially preferred primer combinations according to the different aspects of the invention are as follows:
Amplification mixture 1: Comprising Gly12Ser ARMS primer (SEQ ID No 10), Gly12Asp ARMS primer (SEQ ID No 13), Gly13Asp ARMS primer (SEQ ID No 16), Gly12Ser, Gly12Asp and Gly13Asp Common Amplification "Primer" (SEQ ID No 19), Gln61His ARMS primer (SEQ ID No 17), and Gln61His Amplification "Primer" (SEQ ID No 22).

Amplification mixture 2: Comprising Gly12Cys ARMS primer (SEQ ID No 12), Gly12Ala ARMS primer (SEQ ID No 14), Gly12Cys and Gly12Ala Common Amplification "Primer" (SEQ ID No 20), Gln61Leu ARMS primer (SEQ ID No 18), and Gln61Leu Amplification "Primer" (SEQ ID No 23).

Amplification mixture 3: Comprising Gly12Arg ARMS primer (SEQ ID No 11), Gly12Val ARMS primer (SEQ ID No 15), and Gly12Arg and Gly12Val Common Amplification "Primer" (SEQ ID No 21).

Amplification mixture 4: Comprising Gly12Cys ARMS primer (SEQ ID No 12), Gly12Ala ARMS primer (SEQ ID No 14) and Gly12Cys and Gly12Ala Common Amplification "Primer" (SEQ ID No 20).

Amplification mixture 5: Comprising Gly12Arg ARMS primer (SEQ ID No 11), Gly12Val ARMS primer (SEQ ID No 15), Gly12Arg and Gly12Val Common Amplification "Primer" (SEQ ID No 21), Gln61Leu ARMS primer (SEQ ID No 18) and Gln61Leu Amplification "Primer" (SEQ ID No 23).

All different Amplification mixtures may additionally contain forward and reverse primers for amplification of the Internal and Extraction controls.

The method of the present invention has proven to easily detect amounts of KRAS mutated DNA of from 1 ng to 1 µg. In particular, the method of the present invention has shown to detect without problem, 5 µl of a cell line with 200 ng/µl mutated DNA, as well as serial dilutions of the former up to 0.2 ng/µl.

The limit of detection of the kit of the present invention (CMA kit) is 1,000 copies of mutant KRAS in a 5 µl sample. The sensitivity of detection value of the CMA kit is 1% (see Example 2 below).

Regarding diagnostic parameters, the Diagnostic Sensitivity value of the CMA kit is of from 92.31% to 100% for all KRAS mutations, with the exception of G12C KRAS mutation, whose Diagnostic Sensitivity value is 86.96%.

Specificity value of the CMA kit is of between 99 and 100% for all KRAS mutations, the Diagnostic Specificity value of the native KRAS being 98.51%. (Detailed information of the Diagnostic Parameters of the CMA Kit according to the present invention is to be found in Example 3 below).

A label may be introduced in the DNA amplification product during ARMS amplification to allow further detection; in particular, a label that provides a signal that may be detected by colorimetric methods, by fluorescent methods, or by any labelling method known in the art. The label can be radioactive, chemiluminescent, luminescent and fluorescent agents. In a preferred aspect, the label that is used is biotin. However, any other kind of label known in the art may be used (eg. digoxigenin).

In a preferred aspect, at least one of the primers used is labelled at the 5' end with biotin. Preferably, the amplification primer is labelled.

Furthermore, labelling of amplified DNA may alternatively be achieved by adding modified nucleotides bearing a label (e.g. biotinylated or digoxigenin dUTP derivatives) in the PCR mixture. Radioactive labels may be used, or fluorophores, in certain embodiments.

Alternative methods that may enable detection of the interaction between any amplification product and its corresponding probe, known to the skilled person, including methods that imply labelling of the probe, may be used.

In a preferred embodiment of the present invention, amplification products, previously denatured, are incubated with target-specific probes that hybridize with the amplification products at least in the region corresponding to the 5' tag of nucleotides provided by the specific primer.

In a preferred embodiment, denaturing of amplified DNA can be performed by heating. Other ways to prepare single stranded DNA after amplification may be used as well; for example, chemical means.

In a preferred aspect, the test sample comprising nucleic acids is divided in two or more aliquots, wherein:
one of the aliquots is subjected to amplification with a mixture comprising the primers of SEQ ID NQ 10, SEQ ID NQ 13, SEQ ID NQ 16, SEQ ID NQ 17, SEQ ID No 19 and SEQ ID No 22 (Mixture 1);
another aliquot is subjected to amplification with a mixture comprising the primers of SEQ ID No 12, SEQ ID No 14, SEQ ID No 18, SEQ ID No 20 and SEQ ID No 23 (Mixture 2),
another aliquot is subjected to amplification with a mixture comprising the primers of SEQ ID No 11, SEQ ID No 15 and SEQ ID No 21 (Mixture 3),
or alternatively,
one of the aliquots is subjected to amplification with Mixture 1 of above;
another aliquot is subjected to amplification with a mixture comprising the primers of SEQ ID No 12, SEQ ID No 14 and SEQ ID No 20 (Mixture 4),
another aliquot is subjected to amplification with a mixture comprising the primers of SEQ ID No 11, SEQ ID No 15, SEQ ID No 18, SEQ ID No 21 and SEQ ID No 23 (Mixture 5).

The method further comprises denaturation of any ARMS amplification product obtained, and the subsequent hybridisation of any such product with a microarray comprising one or more of the probes selected from SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54 and SEQ ID No 55.

In a preferred embodiment of the present invention, the probes for detection of amplification products are provided in a microarray. Microarray technology enables simultaneous detection of different amplification products, corresponding to one or more of the KRAS mutations present in a sample, while providing the controls needed to ensure the reliability of the results.

In a preferred embodiment of the present invention, single-stranded DNA obtained from one or more amplification products, is incubated with a plurality of target-specific probes provided on a microarray. At least one, but preferably more than one probe with ability to hybridise with each target sequence, are provided on the microarray. In certain embodiments of the invention, the single-stranded DNA may be incubated with target-specific probes provided in solution; however, it is preferred that the probes are arranged on a microarray.

According to the different aspects of the invention, probes contained in a microarray, which may be placed on a slide or contained in a reaction vessel, which is then called an array vessel. Array vessels may have different formats of presentation, including individual array vessels, such as wells or tubes, or sets of array vessels arranged in strips of wells or tubes, or flat plates. Usually, plates consist of sets of strips of array vessels. Thus, a microarray of the present invention may be contained in an individual array vessel.

Alternatively, two or more microarrays may be contained in a strip of vessels. In a preferred embodiment, the strip of vessels is constituted by 8 vessels. Further, three or more array vessels may be arranged in a set of strip of vessels. In another preferred embodiment, the set of strip of vessels is a microtiter plate. In yet another preferred embodiment, the microtiter plate is constituted by 96 array vessels.

In preferred embodiments, the probes of the microarray may be immobilised on a solid support wherein this solid support can be the bottom of an array vessel or a different solid support attached to the bottom of an array vessel. This means that the surface of the microarray may be the flat bottom of the array vessel. Alternatively, the surface of the microarray may be a solid support attached to the bottom of the array vessel.

In an embodiment of the present invention, the reaction vessel has a typical size for a laboratory reaction vessel. Typical filling volumes lie in the range of 100 µl to 2.5 ml, but can also be lower or higher in special embodiments. The reaction vessel may have a normal filling volume for a standard Eppendorf tube of up to 1.5 ml. Further preferred filling volumes are up to 0.4 ml, up to 0.5 ml, up to 0.7 ml, up to 1.0 ml or up to 2.0 ml.

Due to the labelling of the amplified DNA, wherever sample molecules interact with probe molecules on the surface of the microarray, a reporter reagent binds the label and produces visible signals which may be detected by a detection device. The interacting probe and sample molecules are identified by the location of the signal on the surface of the microarray. In the particular case where sample amplification products are labelled with biotin, the reporter agent can be horseradish peroxidase covalently joined to streptavidin. The latter binds specifically to biotin, and the peroxidase triggers the precipitation of substrates like tetramethylbenzidine (TMB).

Any other reaction that results in a precipitate on array elements, and that can be used to detect the interaction between target and probe molecules according to the present invention may be used.

Any other detection method known in the state of the art, such as fluorescence, may be used for detection of the interaction between amplification products and corresponding probes. The method will be dependent on the exact labelling of the amplification products.

The probes of the present invention can be obtained by different methods, such as chemical synthesis (e. g. by the conventional phosphotriester method) or genetic engineering techniques, for example by molecular cloning of recombinant plasmids in which corresponding nucleotide sequences have been inserted and can be later obtained by digestion with nucleases.

Probes or mixtures of probes specific for each of the 9 KRAS mutations, may be immobilized in a single location of the solid support, in two distinct locations of the solid support and in three or more distinct locations of the solid support. Additionally, one or more control probes are also provided in distinct locations.

In a preferred embodiment, visualization of the interactions between amplification products and their corresponding KRAS specific or control probes, consists of the following steps:
- First, the image of the array is captured using an optical device;
- Then, the image is analysed;
- Finally, a report containing an interpretation of the result is provided.

Preferably, the image is analysed by means of appropriate software. Any device suitable for this processing can be used.

Detection of the 9 KRAS mutations with the method of the present invention is compatible with detection of other mutations in the KRAS gene, as well as of mutations in other genes relevant in cancer. As a matter of fact, the method of the present invention can be combined with other methods of detection of mutations, either in KRAS and/or in any other genes relevant in cancer, for performing a thorough diagnosis and/or prognosis of cancer.

The method of detection of the 9 KRAS mutations Gly12Ser, Gly12Arg, Gly12Cys, Gly12Asp, Gly12Ala, Gly12Val, Gly13Asp, Gln61His and Gln61Leu of the present invention, can be applied to any pathology and to any sample suspicious of correlating with KRAS mutations.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The examples provided below merely illustrate the invention and in no way limit the scope of the accompanying claims.

EXAMPLES

Example 1

The following mixture of reagents was prepared for Multiplex ARMS amplification of the KRAS mutations Gly12Ser, Gly12Asp, Gly13Asp and Gln61 His in samples/cell lines/clones (Multiplex 1):

| Reagents Multiplex 1 | Stock Concentration (µM) | Final Concentration (µM) |
| --- | --- | --- |
| 2X QIAGEN Multiplex PCR Master Mix | 2x | 1x |
| ARMS primer SEQ ID No 10 | 50 | 0.20 |
| ARMS primer SEQ ID No 13 | 50 | 0.20 |
| ARMS primer SEQ ID No 16 | 50 | 0.20 |
| Amplification primer SEQ ID No 19 (Biotin labeled) | 50 | 1.00 |
| ARMS primer SEQ ID No 17 | 50 | 0.20 |
| Amplification primer SEQ ID No 22 (Biotin labeled) | 50 | 0.80 |
| H2O | | Up to 45 ul |

In the same way, mixtures of reagents corresponding to Multiplex 4 and Multiplex 5 were prepared as well.

The total volume per tube is of 45 µl.

Next, 5 µl of a total eluate of 30 µl obtained from paraffin-embedded tissue sections (sample), or from the indicated clones, were added up to a final reaction volume of 50 µl.

| Tube | Sample/Clon | Mutation | Multiplex |
| --- | --- | --- | --- |
| 1 | Sample | G12S | 1 |
| 2 | Sample | G12R | 5 |

-continued

| Tube | Sample/Clon | Mutation | Multiplex |
|------|-------------|----------|-----------|
| 3 | Sample | G12D | 1 |
| 4 | Clon 10e5 | G12C | 4 |
| 5 | Sample | G12V | 5 |
| 6 | Clon 10e5 | G12A | 4 |
| 7 | Sample | G13D | 1 |
| 8 | Sample | Q61L | 5 |
| 9 | Clon 10e4 | Q61H | 1 |
| 10 | H2O | Negative Control | 5 |

The thermal cycling conditions of the PCR were:

| NUMBER OF CYCLES | TEMPERATURE | TIME |
|------------------|-------------|------|
| 1 cycle | 95° C. | 15' |
| 40 cycles | 94° C. | 15" |
|  | 62° C. | 60" |
| 1 cycle | 72° C. | 10' |
| 1 cycle | 4° C. | Forever |

Results of the different Multiplex ARMS amplifications are displayed in FIG. 3. The different ARMS products were visualized in a 2% agarose gel, wherein the products of the different amplification reactions were analysed. In these experiments it has been checked that ARMS amplification only takes place when the sample subjected to ARMS amplification, is that of a sample/clon/cell line, corresponding to one of the KRAS mutations for which ARMS primers have been included in the mixture of reagents used for Multiplex amplification.

As it can be observed in FIG. 3 the ARMS amplification products corresponding to the different mutations, are present in wells of samples or clones of such mutations; It has also been confirmed by DNA sequencing that the ARMS products obtained really result from the specific amplification of the sample or clon, with the corresponding ARMS primer.

It has also been confirmed that no ARMS amplification product was to be found in samples/clones/cell lines corresponding to mutations not included in each Multiplex (not shown). ARMS amplification in each Multiplex is thereby specific.

The different Multiplex ARMS amplification products where denatured and hybridized with microarrays of probes. Visualization of the corresponding results is displayed in FIGS. 4A and 4B.

It has also been checked that inclusion of the forward and reverse primers that are necessary for Internal Control and Extraction Control amplification, as well as of a plasmid such as PPG44, also necessary for Internal Control amplification, at the concentrations displayed below, does not alter the obtained results:

| Reagents Multiplex 1/2/3/4/5 | Stock Concentration (μM) | Final Concentration (μM) |
|---|---|---|
| IC forward primer | 50 | 0.20 |
| IC reverse primer (Biotin labeled) | 50 | 0.20 |
| EC forward primer | 50 | 0.20 |
| EC reverse primer (Biotin labeled) | 50 | 0.20 |
| Plasmid PPG44 | 7.5 fg | 0.25 |

IC: Internal Control; EC: Extraction Control.

Example 2

Clones of the different KRAS mutations were prepared, and detection of different dilutions of these clones was tested, both with the kit of the present invention (CMA), and with a Gold Standard Kit (TheraScreen® K-RAS Mutation Kit of Qiagen).

The dilutions tested included 100,000; 10,000; 1,000; 100; and 10 copies in 5 μl of clones of the different KRAS mutations. Some representative results of this comparison between the CMA and TheraScreen kits are to be found in FIG. 5.

Basically, the dilution corresponding to 1,000 copies of any of the KRAS mutations was detected without problem with the CMA kit. Displayed in FIG. 5a) is the result obtained with 1,000 copies in 5 μl of the clon of G12R KRAS mutation.

Results of detection of 10, 100 and 1,000 copies of a G12R KRAS clone in 5 μl with the Gold Standard kit, TheraScreen of Qiagen, are shown in FIG. 5b). The TheraScreen Kit of Qiagen is based on Scorpions real-time assays. These assays use the number of PCR cycles necessary to detect a fluorescent signal above a background signal, as a measure of the target molecules present at the beginning of the reaction. The point at which the signal is detected above background fluorescence is called the 'cycle threshold' (Ct).

Sample ΔCt values are calculated as the difference between the mutation assay Ct and control assay Ct from the same sample. Samples are classed as mutation positive if they give a ΔCt less than the 1% ΔCt value for that assay. Above this value, the sample may either contain less than 1% mutation (beyond the limit of the assays), or the sample is mutation negative.

The Kit TheraScreen of Qiagen relies also in a LightCycler® 480 Adapt Software, which calculates ΔCt values and determines whether a sample is mutation positive or negative based on 1% cut-off values which are different for each KRAS mutation:

| Assay | 1% delta Ct |
|-------|-------------|
| 12ALA | 6.25 |
| 12ASP | 7.72 |
| 12ARG | 6.83 |
| 12CYS | 6.95 |
| 12SER | 8.95 |
| 12VAL | 6.50 |
| 13ASP | 9.09 |

From the graph displayed in 4b), the Ct values corresponding to 10, 100 and 1,000 copies of the G12R KRAS clone were obtained. Those corresponding to 10 and 100 copies of the G12R KRAS clone were much too high, only the dilution corresponding to 1,000 copies of the G12R KRAS clone in 5 μl providing a positive result with the TheraScreen kit of Qiagen.

FIG. 5c) is a Table with the different results obtained with the CMA and TheraScreen kits, for different dilutions of clones corresponding to the different indicated KRAS mutations.

As regards TheraScreen kit results, Ct values corresponding to the different KRAS mutations are displayed. As regards results with the CMA kit, "+" and "−" represent positive and negative detection results, respectively.

The results of the present experiments can be summarized in that the limit of detection of the CMA kit is 1,000 copies of mutant KRAS in 5 μl, the limit of detection of the TheraScreen kit also being of 1,000 copies in 5 μl for most KRAS mutations. Detection abilities of CMA and TheraScreen kits are thereby equivalent, the sensitivity of detection value of the CMA kit being also comparable to that of the TheraScreen kit, the value being of 1%.

Example 3

Diagnostic parameters including diagnostic Sensitivity, diagnostic Specificity, Positive Predictive Value and Negative Predictive Value, of the CMA kit of the present invention, were obtained for the different KRAS mutations. The total number of samples that were tested is of 376 real samples.

| KRAS Mutation | N = 376 | Sensitivity | Specificity | PPV | NPV |
|---|---|---|---|---|---|
| G12A | 25 | 96.00 | 99.48 | 92.31 | 99.74 |
| G12C | 23 | 86.96 | 100.00 | 100.00 | 99.23 |
| G12D | 68 | 98.53 | 99.71 | 98.53 | 99.71 |
| G12V | 52 | 92.31 | 100.00 | 100.00 | 98.89 |
| G12R | 7 | 100.00 | 99.75 | 87.50 | 100.00 |
| G12S | 25 | 96.00 | 100.00 | 100.00 | 99.74 |
| G13D | 39 | 92.31 | 100.00 | 100.00 | 99.19 |
| Q61H | 3 | 100.00 | 100.00 | 100.00 | 100.00 |
| Q61L | 2 | 100.00 | 100.00 | 100.00 | 100.00 |
| Native | 132 | ND | 98.51 | ND | 97.06 |

ND: Non-determined. There is no point in determining Sensitivity and PPV values in case of native KRAS.

Example 4

1 ng of cell line NCI-H460 (Gly12Ser negative), 1 ng of cell line HCT 116 (Gly12Ser negative) and 1 ng of cell line A549 (Gly12Ser positive), were individually subjected to amplification with an amplification mixture comprising ARMS and amplification primers corresponding to Gly12Ser KRAS mutation. The thermal cycling conditions that were used where as follows:

| NUMBER OF CYCLES | TEMPERATURE | TIME |
|---|---|---|
| 1 cycle | 95° C. | 15' |
| 40 cycles | 94° C. | 15" |
| | 54° C. or 62° C. | 60" |
| 1 cycle | 72° C. | 10' |
| 1 cycle | 4° C. | Forever |

Analysis of the amplification products corresponding to KRAS mutation Gly12Ser, obtained at the two different hybridization temperatures 54° C. and 62° C., as visualized after agarose gel electrophoresis, is displayed in FIG. 6 below.

As it can be observed in FIG. 6, amplification specificity of the KRAS mutation Gly12Ser is only achieved under the amplification conditions whose hybridization temperature is 62° C., while at amplification conditions whose hybridization temperature is 54° C., non-specific amplification of Gly12Ser takes place.

Thus, while at hybridization temperature of 62° C., only the cell line positive for Gly12Ser, A549, yields the amplification product corresponding to Gly12Ser, and the other two cell lines that are negative for Gly12Ser (NCI-H460 and HCT 116) do not yield any such amplification product, at hybridization temperature of 54° C. all three cell lines provide an amplification product corresponding to Gly12Ser. The presence of the amplification product corresponding to Gly12Ser in cell lines negative for Gly12Ser is due to a non-specific amplification.

The invention claimed is:

1. A method for detecting one or more KRAS mutations selected from Gly12Ser, Gly12Arg, Gly12Cys, Gly12Asp, Gly12Ala, Gly12Val, Gly13Asp, Gln61His and Gln61Leu in a test sample comprising nucleic acid, wherein said method comprises subjecting the sample to amplification with a mixture comprising one or more ARMS primers selected from the group consisting of SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, the mixture further comprising one or more amplification primers selected from the group consisting of SEQ ID No 19, SEQ ID No 20, SEQ ID No 21, SEQ ID No 22 and SEQ ID No 23, wherein one, two, three, four or five of the following primer combinations are used:
   a) SEQ ID No 10, SEQ ID No 13, SEQ ID No 16, SEQ ID No 17, SEQ ID No 19 and SEQ ID No 22 (Mixture 1);
   b) SEQ ID No 12, SEQ ID No 14, SEQ ID No 18, SEQ ID No 20 and SEQ ID No 23 (Mixture 2);
   c) SEQ ID No 11, SEQ ID No 15 and SEQ ID No 21 (Mixture 3);

d) SEQ ID No 12, SEQ ID No 14 and SEQ ID No 20 (Mixture 4); and
e) SEQ ID No 11, SEQ ID No 15, SEQ ID No 18, SEQ ID No 21 and SEQ ID No 23 (Mixture 5).

2. The method of claim 1 wherein the amplification is performed at a hybridization temperature of from about 60° C. to about 64° C.

3. The method of claim 1 wherein the amplification is carried out under the following thermal cycling conditions:

| NUMBER OF CYCLES | TEMPERATURE | TIME |
|---|---|---|
| 1 cycle | 95° C. | 15' |
| ≥40 cycles | 94° C. | 15-30" |
|  | 60-64° C. | 45-90" |
| 1 cycle | 62-72° C. | 6-12' |
| 1 cycle | 4° C. | Forever. |

4. The method of claim 1 wherein the one or more amplification primers which are combined with one or more ARMS primers comprise from 17 to 35 nucleotides, and are such that, when combined with the one or more ARMS primers, amplification results in one or more products of 1,000 bp or shorter.

5. The method of claim 1 wherein one or more amplification products obtained are contacted with one or more probes, each probe specifically hybridising to a region in the product corresponding to a 5' tag sequence of the corresponding ARMS primer.

6. The method of claim 5 wherein the one or more probes with which the amplification products are contacted have a length of from 17 to 39 nucleotides, the region of the probe which specifically hybridizes to the region in the product corresponding to the 5' tag sequence of the ARMS primer having a length of from 17 to 30 nucleotides.

7. The method of claim 5 wherein the one or more probes comprise sequences selected from the group consisting of SEQ ID No 24, SEQ ID No 25, SEQ ID No 26, SEQ ID No 27, SEQ ID No 28, SEQ ID No 29, SEQ ID No 30, SEQ ID No 31 and SEQ ID No 32.

8. The method of claim 5 wherein the one or more probes are selected from the group consisting of SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54 and SEQ ID No 55.

9. A kit for detecting one or more KRAS mutations selected from the group consisting of Gly12Ser, Gly12Arg, Gly12Cys, Gly12Asp, Gly12Ala, Gly12Val, Gly13Asp, Gln61His and Gln61Leu in a test sample comprising nucleic acid, wherein said kit comprises one or more of the following amplification mixtures:
a) an amplification mixture comprising primers of SEQ ID No 10, SEQ ID No 13, SEQ ID No 16, SEQ ID No 17, SEQ ID No 19 and SEQ ID No 22 (Mixture 1);
b) an amplification mixture comprising primers of SEQ ID No 12, SEQ ID No 14, SEQ ID No 18, SEQ ID No 20 and SEQ ID No 23 (Mixture 2);
c) an amplification mixture comprising primers of SEQ ID No 11, SEQ ID No 15 and SEQ ID No 21 (Mixture 3);
d) an amplification mixture comprising primers of SEQ ID No 12, SEQ ID No 14 and SEQ ID No 20 (Mixture 4); and
e) an amplification mixture comprising primers of SEQ ID No 11, SEQ ID No 15 SEQ ID No 18, SEQ ID No 21 and SEQ ID No 23 (Mixture 5),
the kit further comprising a microarray wherein one or more probes that specifically bind to ARMS products of one or more of the KRAS mutations Gly12Ser, Gly12Arg, Gly12Cys, Gly12Asp, Gly12Ala, Gly12Val, Gly13Asp, Gln61His and Gln61Leu, are immobilised, each probe specifically hybridising to a region in the corresponding ARMS product complementary to a 5' tag sequence of the corresponding ARMS primer.

10. The kit of claim 9 wherein one or more probes have a length of from 17 to 39 nucleotides, and comprise one or more sequences selected from the group consisting of SEQ ID No 24, SEQ ID No 25, SEQ ID No 26, SEQ ID No 27, SEQ ID No 28, SEQ ID No 29, SEQ ID No 30, SEQ ID No 31 and SEQ ID No 32.

11. The kit of claim 9 wherein said kit further comprises a microarray comprising one or more probes selected from the group consisting of SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54 and SEQ ID No 55.

12. A combination of primers selected from the group consisting of:
a) SEQ ID No 10, SEQ ID No 13, SEQ ID No 16, SEQ ID No 17, SEQ ID No 19 and SEQ ID No 22 (Mixture 1);
b) SEQ ID No 12, SEQ ID No 14, SEQ ID No 18, SEQ ID No 20 and SEQ ID No 23 (Mixture 2);
c) SEQ ID No 11, SEQ ID No 15 and SEQ ID No 21 (Mixture 3);
d) SEQ ID No 12, SEQ ID No 14 and SEQ ID No 20 (Mixture 4); and
e) SEQ ID No 11, SEQ ID No 15, SEQ ID No 18, SEQ ID No 21 and SEQ ID No 23 (Mixture 5).

13. A method for diagnosing a pathologic condition in a patient, prognosing a pathologic condition in a patient, or predicting a response of a patient to therapy with anti-EGFR antibodies using the method of claim 1.

14. A method for diagnosing a pathologic condition in a patient, prognosing a pathologic condition in a patient, or predicting a response of a patient to therapy with anti-EGFR antibodies, comprising detecting one or more KRAS mutations using the kit of claim 9.

15. A method for diagnosing a pathologic condition in a patient, prognosing a pathologic condition in a patient, or predicting a response of a patient to therapy with anti-EGFR antibodies, comprising detecting one or more KRAS mutations using a combination of primers of claim 12.

16. The method of claim 2 wherein amplification is carried out under the following thermal cycling conditions:

| NUMBER OF CYCLES | TEMPERATURE | TIME |
|---|---|---|
| 1 cycle | 95° C. | 15' |
| 40-42 cycles | 94° C. | 15" |
|  | 62° C. | 60" |
| 1 cycle | 72° C. | 10' |
| 1 cycle | 4° C. | Forever. |

17. A method for detecting one or more KRAS mutations selected from Gly12Ser, Gly12Arg, Gly12Cys, Gly12Asp, Gly12Ala, Gly12Val, Gly13Asp, Gln61His and Gln61Leu in a test sample comprising nucleic acid, wherein said method comprises subjecting the sample to amplification with a mixture comprising one or more ARMS primers selected from the group consisting of SEQ ID No 10, SEQ ID No 11, SEQ ID No 12, SEQ ID No 13, SEQ ID No 14, SEQ ID No 15, SEQ ID No 16, SEQ ID No 17 and SEQ ID No 18, the mixture further comprising one or more amplification primers, wherein one or more amplification products are obtained, and wherein the one or more amplification products are contacted with a probe comprising SEQ ID No 33.

* * * * *

UNITED STATES PATENT AND TRADEMARK OFFICE
CERTIFICATE OF CORRECTION

Page 1 of 2

PATENT NO. : 10,023,904 B2
APPLICATION NO. : 14/367770
DATED : July 17, 2018
INVENTOR(S) : Maria Luisa Villahermosa Jaen and Juan Moscoso del Prado It is certified that error appears in the above-identified patent and that said Letters Patent is hereby corrected as shown below:

In the Claims

In Claim 1, Column 41, Line numbers 64-66, replace every occurrence of "SEQ ID No" with -- SEQ ID NO: --.

In Claim 1, Column 42, Line numbers 56-58, replace every occurrence of "SEQ ID No" with -- SEQ ID NO: --.

In Claim 1, Column 42, Line numbers 61-66, replace every occurrence of "SEQ ID No" with -- SEQ ID NO: --.

In Claim 1, Column 43, Line numbers 1-4, replace every occurrence of "SEQ ID No" with -- SEQ ID NO: --.

In Claim 7, Column 43, Line numbers 39-41, replace every occurrence of "SEQ ID No" with -- SEQ ID NO: --.

In Claim 8, Column 43, Line numbers 43-49, replace every occurrence of "SEQ ID No" with -- SEQ ID NO: --.

In Claim 9, Column 43, Line numbers 56-66, replace every occurrence of "SEQ ID No" with -- SEQ ID NO: --.

In Claim 9, Column 44, Line numbers 1-3, replace every occurrence of "SEQ ID No" with -- SEQ ID NO: --.

In Claim 10, Column 44, Line numbers 14-17, replace every occurrence of "SEQ ID No" with -- SEQ ID NO: --.

Signed and Sealed this
Second Day of October, 2018

Andrei Iancu
*Director of the United States Patent and Trademark Office*

In Claim 11, Column 44, Line numbers 20-26, replace every occurrence of "SEQ ID No" with -- SEQ ID NO: --.

In Claim 12, Column 44, Line numbers 29-39, replace every occurrence of "SEQ ID No" with -- SEQ ID NO: --.

In Claim 17, Column 45, Line numbers 4-6, replace every occurrence of "SEQ ID No" with -- SEQ ID NO: --.

In Claim 17, Column 45, Line 10, replace "SEQ ID No 33." with -- SEQ ID NO: 33. --.

SEQUENCE LISTING

```
<160> NUMBER OF SEQ ID NOS: 55

<210> SEQ ID NO 1
<211> LENGTH: 30
<212> TYPE: DNA
<213> ORGANISM: Artificial Sequence
<220> FEATURE:
<223> OTHER INFORMATION: 3' sequence of ARMS primer for amplification of
      KRAS mutation Gly12Ser, the sequence being target-specific

<400> SEQUENCE: 1
ctgaatataa acttgtggta gttggcgcta                                    30

<210> SEQ ID NO 2
<211> LENGTH: 27
<212> TYPE: DNA
<213> ORGANISM: Artificial Sequence
<220> FEATURE:
<223> OTHER INFORMATION: 3' sequence of ARMS primer for amplification of
      KRAS mutation Gly12Arg, the sequence being target-specific

<400> SEQUENCE: 2
cgtcaaggca ctcttgccta cgacacg                                       27

<210> SEQ ID NO 3
<211> LENGTH: 30
<212> TYPE: DNA
<213> ORGANISM: Artificial Sequence
<220> FEATURE:
<223> OTHER INFORMATION: 3' sequence of ARMS primer for amplification of
```

KRAS mutation Gly12Cys, the sequence being target-specific

<400> SEQUENCE: 3
ctgaatataa acttgtggta gttggagatt                                        30

<210> SEQ ID NO 4
<211> LENGTH: 31
<212> TYPE: DNA
<213> ORGANISM: Artificial Sequence
<220> FEATURE:
<223> OTHER INFORMATION: 3' sequence of ARMS primer for amplification of
      KRAS mutation Gly12Asp, the sequence being target-specific

<400> SEQUENCE: 4
ctgaatataa acttgtggta gttggagccg a                                      31

<210> SEQ ID NO 5
<211> LENGTH: 31
<212> TYPE: DNA
<213> ORGANISM: Artificial Sequence
<220> FEATURE:
<223> OTHER INFORMATION: 3' sequence of ARMS primer for amplification of
      KRAS mutation Gly12Ala, the sequence being target-specific

<400> SEQUENCE: 5
ctgaatataa acttgtggta gttgcagatg c                                      31

<210> SEQ ID NO 6
<211> LENGTH: 26
<212> TYPE: DNA
<213> ORGANISM: Artificial Sequence
<220> FEATURE:
<223> OTHER INFORMATION: 3' sequence of ARMS primer for amplification of
      KRAS mutation Gly12Val, the sequence being target-specific

<400> SEQUENCE: 6
cgtcaaggca ctcttgccta cggcaa                                            26

<210> SEQ ID NO 7
<211> LENGTH: 34
<212> TYPE: DNA
<213> ORGANISM: Artificial Sequence
<220> FEATURE:
<223> OTHER INFORMATION: 3' sequence of ARMS primer for amplification of
      KRAS mutation Gly13Asp, the sequence being target-specific

<400> SEQUENCE: 7
ctgaatataa acttgtggta gttggagctg ggga                                   34

<210> SEQ ID NO 8
<211> LENGTH: 27
<212> TYPE: DNA
<213> ORGANISM: Artificial Sequence
<220> FEATURE:
<223> OTHER INFORMATION: 3' sequence of ARMS primer for amplification of
      KRAS mutation Gln61His, the sequence being target-specific

<400> SEQUENCE: 8
tggtccctca ttgcactgta ctccaca                                           27

<210> SEQ ID NO 9
<211> LENGTH: 23
<212> TYPE: DNA
<213> ORGANISM: Artificial Sequence
<220> FEATURE:
<223> OTHER INFORMATION: 3' sequence of ARMS primer for amplification of
      KRAS mutation Gln61Leu, the sequence being target-specific

<400> SEQUENCE: 9
gatattctcg acacagcagt tct                                           23

<210> SEQ ID NO 10
<211> LENGTH: 47
<212> TYPE: DNA
<213> ORGANISM: Artificial Sequence
<220> FEATURE:
<223> OTHER INFORMATION: ARMS primer for amplification of KRAS mutation
      Gly12Ser

<400> SEQUENCE: 10
aaggataatt aattaatctg aatataaact tgtggtagtt ggcgcta                 47

<210> SEQ ID NO 11
<211> LENGTH: 44
<212> TYPE: DNA
<213> ORGANISM: Artificial Sequence
<220> FEATURE:
<223> OTHER INFORMATION: ARMS primer for amplification of KRAS mutation
      Gly12Arg

<400> SEQUENCE: 11
aatattgagg ctgcagccgt caaggcactc ttgcctacga cacg                    44

<210> SEQ ID NO 12
<211> LENGTH: 49
<212> TYPE: DNA
<213> ORGANISM: Artificial Sequence
<220> FEATURE:
<223> OTHER INFORMATION: ARMS primer for amplification of KRAS mutation
      Gly12Cys

<400> SEQUENCE: 12
ggctagctag ccgcggtagc tgaatataaa cttgtggtag ttggagatt               49

<210> SEQ ID NO 13
<211> LENGTH: 49
<212> TYPE: DNA
<213> ORGANISM: Artificial Sequence
<220> FEATURE:
<223> OTHER INFORMATION: ARMS primer for amplification of KRAS mutation
      Gly12Asp

<400> SEQUENCE: 13
cggtatttgg gcaacctgct gaatataaac ttgtggtagt tggagccga               49

<210> SEQ ID NO 14
<211> LENGTH: 50
<212> TYPE: DNA
<213> ORGANISM: Artificial Sequence
<220> FEATURE:
<223> OTHER INFORMATION: ARMS primer for amplification of KRAS mutation
      Gly12Ala

<400> SEQUENCE: 14
gaatccatgt gatgacttgc tgaatataaa cttgtggtag ttgcagatgc              50

<210> SEQ ID NO 15
<211> LENGTH: 45
<212> TYPE: DNA
<213> ORGANISM: Artificial Sequence
<220> FEATURE:
<223> OTHER INFORMATION: ARMS primer for amplification of KRAS mutation
      Gly12Val

<400> SEQUENCE: 15
tcaggcggcc aggatggagc gtcaaggcac tcttgcctac ggcaa                45

<210> SEQ ID NO 16
<211> LENGTH: 53
<212> TYPE: DNA
<213> ORGANISM: Artificial Sequence
<220> FEATURE:
<223> OTHER INFORMATION: ARMS primer for amplification of KRAS mutation
      Gly13Asp

<400> SEQUENCE: 16
ccgagacgtt cgacactgcc tgaatataaa cttgtggtag ttggagctgg gga         53

<210> SEQ ID NO 17
<211> LENGTH: 47
<212> TYPE: DNA
<213> ORGANISM: Artificial Sequence
<220> FEATURE:
<223> OTHER INFORMATION: ARMS primer for amplification of KRAS mutation
      Gln61His

<400> SEQUENCE: 17
ttaggctctg aactcggcgt tggtccctca ttgcactgta ctccaca                47

<210> SEQ ID NO 18
<211> LENGTH: 42
<212> TYPE: DNA
<213> ORGANISM: Artificial Sequence
<220> FEATURE:
<223> OTHER INFORMATION: ARMS primer for amplification of KRAS mutation
      Gln61Leu

<400> SEQUENCE: 18
ggccacttac cgggatccag atattctcga cacagcagtt ct                     42

<210> SEQ ID NO 19
<211> LENGTH: 22
<212> TYPE: DNA
<213> ORGANISM: Artificial Sequence
<220> FEATURE:
<223> OTHER INFORMATION: Amplification primer to be used in combination
      with any of ARMS primers comprising SEQ ID NO 1,
      4, 7, or consisting of SEQ ID NO 10, 13, 16

<400> SEQUENCE: 19
ggtcctgcac cagtaatatg ca                                           22

<210> SEQ ID NO 20
<211> LENGTH: 22
<212> TYPE: DNA
<213> ORGANISM: Artificial Sequence
<220> FEATURE:
<223> OTHER INFORMATION: Amplification primer to be used in combination
      with any of ARMS primers comprising SEQ ID NO 3,
      5, or ARMS primers consisting of SEQ ID NO 12, 14

<400> SEQUENCE: 20
ggtcctgcac cagtaatatg ca                                           22

<210> SEQ ID NO 21
<211> LENGTH: 21
<212> TYPE: DNA
<213> ORGANISM: Artificial Sequence
<220> FEATURE:
<223> OTHER INFORMATION: Amplification primer to be used in combination
      with any of ARMS primers comprising SEQ ID NO 2, 6, or ARMS primers consisting of SEQ ID NO 11, 15

<400> SEQUENCE: 21
ggtggagtat tgatagtgt a                                              21

<210> SEQ ID NO 22
<211> LENGTH: 24
<212> TYPE: DNA
<213> ORGANISM: Artificial Sequence
<220> FEATURE:
<223> OTHER INFORMATION: Amplification primer to be used in combination
      with any of ARMS primer comprising SEQ ID NO 8, or
      ARMS primer consisting of SEQ ID NO 17

<400> SEQUENCE: 22
gtttctccct tctcaggatt ccta                                          24

<210> SEQ ID NO 23
<211> LENGTH: 24
<212> TYPE: DNA
<213> ORGANISM: Artificial Sequence
<220> FEATURE:
<223> OTHER INFORMATION: Amplification primer to be used in combination
      with any of ARMS primer comprising SEQ ID NO 9, or
      ARMS primer consisting of SEQ ID NO 18

<400> SEQUENCE: 23
gggatattac ctacctcata aaca                                          24

<210> SEQ ID NO 24
<211> LENGTH: 17
<212> TYPE: DNA
<213> ORGANISM: Artificial Sequence
<220> FEATURE:
<223> OTHER INFORMATION: 5' sequence of ARMS primer for amplification of
      KRAS mutation Gly12Ser, the sequence being non-target-specific.

<400> SEQUENCE: 24
aaggataatt aattaat                                                  17

<210> SEQ ID NO 25
<211> LENGTH: 17
<212> TYPE: DNA
<213> ORGANISM: Artificial Sequence
<220> FEATURE:
<223> OTHER INFORMATION: 5' sequence of ARMS primer for amplification of
      KRAS mutation Gly12Arg, the sequence being non-target-specific.

<400> SEQUENCE: 25
aatattgagg ctgcagc                                                  17

<210> SEQ ID NO 26
<211> LENGTH: 19
<212> TYPE: DNA
<213> ORGANISM: Artificial Sequence
<220> FEATURE:
<223> OTHER INFORMATION: 5' sequence of ARMS primer for amplification of
      KRAS mutation Gly12Cys, the sequence being non-target-specific.

<400> SEQUENCE: 26
ggctagctag ccgcggtag                                                19

<210> SEQ ID NO 27
<211> LENGTH: 18
<212> TYPE: DNA
<213> ORGANISM: Artificial Sequence
<220> FEATURE:

<223> OTHER INFORMATION: 5' sequence of ARMS primer for amplification of
      KRAS mutation Gly12Asp, the sequence being non-target-specific.

<400> SEQUENCE: 27
cggtatttgg gcaacctg                                                    18

<210> SEQ ID NO 28
<211> LENGTH: 19
<212> TYPE: DNA
<213> ORGANISM: Artificial Sequence
<220> FEATURE:
<223> OTHER INFORMATION: 5' sequence of ARMS primer for amplification of
      KRAS mutation Gly12Ala, the sequence being non-target-specific.

<400> SEQUENCE: 28
gaatccatgt gatgacttg                                                   19

<210> SEQ ID NO 29
<211> LENGTH: 19
<212> TYPE: DNA
<213> ORGANISM: Artificial Sequence
<220> FEATURE:
<223> OTHER INFORMATION: 5' sequence of ARMS primer for amplification of
      KRAS mutation Gly12Val, the sequence being non-target-specific.

<400> SEQUENCE: 29
tcaggcggcc aggatggag                                                   19

<210> SEQ ID NO 30
<211> LENGTH: 19
<212> TYPE: DNA
<213> ORGANISM: Artificial Sequence
<220> FEATURE:
<223> OTHER INFORMATION: 5' sequence of ARMS primer for amplification of
      KRAS mutation Gly13Asp, the sequence being non-target-specific.

<400> SEQUENCE: 30
ccgagacgtt cgacactgc                                                   19

<210> SEQ ID NO 31
<211> LENGTH: 20
<212> TYPE: DNA
<213> ORGANISM: Artificial Sequence
<220> FEATURE:
<223> OTHER INFORMATION: 5' sequence of ARMS primer for amplification of
      KRAS mutation Gln61His, the sequence being non-target-specific.

<400> SEQUENCE: 31
ttaggctctg aactcggcgt                                                  20

<210> SEQ ID NO 32
<211> LENGTH: 19
<212> TYPE: DNA
<213> ORGANISM: Artificial Sequence
<220> FEATURE:
<223> OTHER INFORMATION: 5' sequence of ARMS primer for amplification of
      KRAS mutation Gln61Leu, the sequence being non-target-specific.

<400> SEQUENCE: 32
ggccacttac cgggatcca                                                   19

<210> SEQ ID NO 33
<211> LENGTH: 30
<212> TYPE: DNA
<213> ORGANISM: Artificial Sequence
<220> FEATURE:
<223> OTHER INFORMATION: Probe for detection of ARMS amplification product of KRAS mutation Gly12Ser

<400> SEQUENCE: 33
gcttgccccg gggaaggata attaattaat        30

<210> SEQ ID NO 34
<211> LENGTH: 25
<212> TYPE: DNA
<213> ORGANISM: Artificial Sequence
<220> FEATURE:
<223> OTHER INFORMATION: Probe for detection of ARMS amplification
      product of KRAS mutation Gly12Ser

<400> SEQUENCE: 34
ccccggggaa ggataattaa ttaat        25

<210> SEQ ID NO 35
<211> LENGTH: 35
<212> TYPE: DNA
<213> ORGANISM: Artificial Sequence
<220> FEATURE:
<223> OTHER INFORMATION: Probe for detection of ARMS amplification
      product of KRAS mutation Gly12Arg

<400> SEQUENCE: 35
ttcgccgggt tacccgggaa tattgaggct gcagc        35

<210> SEQ ID NO 36
<211> LENGTH: 30
<212> TYPE: DNA
<213> ORGANISM: Artificial Sequence
<220> FEATURE:
<223> OTHER INFORMATION: Probe for detection of ARMS amplification
      product of KRAS mutation Gly12Arg

<400> SEQUENCE: 36
cgggttaccc gggaatattg aggctgcagc        30

<210> SEQ ID NO 37
<211> LENGTH: 25
<212> TYPE: DNA
<213> ORGANISM: Artificial Sequence
<220> FEATURE:
<223> OTHER INFORMATION: Probe for detection of ARMS amplification
      product of KRAS mutation Gly12Cys

<400> SEQUENCE: 37
ggctagctag ccgcggtagc tgaat        25

<210> SEQ ID NO 38
<211> LENGTH: 38
<212> TYPE: DNA
<213> ORGANISM: Artificial Sequence
<220> FEATURE:
<223> OTHER INFORMATION: Probe for detection of ARMS amplification
      product of KRAS mutation Gly12Cys

<400> SEQUENCE: 38
cgaggccttg gccggctagc tagccgcggt agctgaat        38

<210> SEQ ID NO 39
<211> LENGTH: 32
<212> TYPE: DNA
<213> ORGANISM: Artificial Sequence
<220> FEATURE:
<223> OTHER INFORMATION: Probe for detection of ARMS amplification
      product of KRAS mutation Gly12Cys -continued

<400> SEQUENCE: 39
cgaggccttg gccggctagc tagccgcggt ag                                  32

<210> SEQ ID NO 40
<211> LENGTH: 33
<212> TYPE: DNA
<213> ORGANISM: Artificial Sequence
<220> FEATURE:
<223> OTHER INFORMATION: Probe for detection of ARMS amplification
      product of KRAS mutation Gly12Cys

<400> SEQUENCE: 40
ccttggccgg ctagctagcc gcggtagctg aat                                 33

<210> SEQ ID NO 41
<211> LENGTH: 27
<212> TYPE: DNA
<213> ORGANISM: Artificial Sequence
<220> FEATURE:
<223> OTHER INFORMATION: Probe for detection of ARMS amplification
      product of KRAS mutation Gly12Cys

<400> SEQUENCE: 41
ccttggccgg ctagctagcc gcggtag                                        27

<210> SEQ ID NO 42
<211> LENGTH: 31
<212> TYPE: DNA
<213> ORGANISM: Artificial Sequence
<220> FEATURE:
<223> OTHER INFORMATION: Probe for detection of ARMS amplification
      product of KRAS mutation Gly12Asp

<400> SEQUENCE: 42
gcttgccccg gggcggtatt tgggcaacct g                                   31

<210> SEQ ID NO 43
<211> LENGTH: 26
<212> TYPE: DNA
<213> ORGANISM: Artificial Sequence
<220> FEATURE:
<223> OTHER INFORMATION: Probe for detection of ARMS amplification
      product of KRAS mutation Gly12Asp

<400> SEQUENCE: 43
ccccggggcg gtatttgggc aacctg                                         26

<210> SEQ ID NO 44
<211> LENGTH: 19
<212> TYPE: DNA
<213> ORGANISM: Artificial Sequence
<220> FEATURE:
<223> OTHER INFORMATION: Probe for detection of ARMS amplification
      product of KRAS mutation Gly12Ala

<400> SEQUENCE: 44
gaatccatgt gatgacttg                                                 19

<210> SEQ ID NO 45
<211> LENGTH: 24
<212> TYPE: DNA
<213> ORGANISM: Artificial Sequence
<220> FEATURE:
<223> OTHER INFORMATION: Probe for detection of ARMS amplification
      product of KRAS mutation Gly12Ala

```
<400> SEQUENCE: 45
gaatccatgt gatgacttga cttg                                              24

<210> SEQ ID NO 46
<211> LENGTH: 38
<212> TYPE: DNA
<213> ORGANISM: Artificial Sequence
<220> FEATURE:
<223> OTHER INFORMATION: Probe for detection of ARMS amplification
      product of KRAS mutation Gly12Ala

<400> SEQUENCE: 46
cgggttaccc gggagtctcg aatccatgtg atgacttg                               38

<210> SEQ ID NO 47
<211> LENGTH: 32
<212> TYPE: DNA
<213> ORGANISM: Artificial Sequence
<220> FEATURE:
<223> OTHER INFORMATION: Probe for detection of ARMS amplification
      product of KRAS mutation Gly12Ala

<400> SEQUENCE: 47
cgggttaccc ggggaatcca tgtgatgact tg                                     32

<210> SEQ ID NO 48
<211> LENGTH: 25
<212> TYPE: DNA
<213> ORGANISM: Artificial Sequence
<220> FEATURE:
<223> OTHER INFORMATION: Probe for detection of ARMS amplification
      product of KRAS mutation Gly12Val

<400> SEQUENCE: 48
tcaggcggcc aggatggagc tgaat                                             25

<210> SEQ ID NO 49
<211> LENGTH: 32
<212> TYPE: DNA
<213> ORGANISM: Artificial Sequence
<220> FEATURE:
<223> OTHER INFORMATION: Probe for detection of ARMS amplification
      product of KRAS mutation Gly12Val

<400> SEQUENCE: 49
cgggttaccc gggtcaggcg gccaggatgg ag                                     32

<210> SEQ ID NO 50
<211> LENGTH: 25
<212> TYPE: DNA
<213> ORGANISM: Artificial Sequence
<220> FEATURE:
<223> OTHER INFORMATION: Probe for detection of ARMS amplification
      product of KRAS mutation Gly13Asp

<400> SEQUENCE: 50
ccgagacgtt cgacactgcc tgaat                                             25

<210> SEQ ID NO 51
<211> LENGTH: 33
<212> TYPE: DNA
<213> ORGANISM: Artificial Sequence
<220> FEATURE:
<223> OTHER INFORMATION: Probe for detection of ARMS amplification
      product of KRAS mutation Gln61His

<400> SEQUENCE: 51
```

```
cggggttaccc gggttaggct ctgaactcgg cgt                    33
```

<210> SEQ ID NO 52
<211> LENGTH: 39
<212> TYPE: DNA
<213> ORGANISM: Artificial Sequence
<220> FEATURE:
<223> OTHER INFORMATION: Probe for detection of ARMS amplification
      product of KRAS mutation Gln61His

<400> SEQUENCE: 52

```
cggggttaccc gggagtctct taggctctga actcggcgt              39
```

<210> SEQ ID NO 53
<211> LENGTH: 32
<212> TYPE: DNA
<213> ORGANISM: Artificial Sequence
<220> FEATURE:
<223> OTHER INFORMATION: Probe for detection of ARMS amplification
      product of KRAS mutation Gln61Leu

<400> SEQUENCE: 53

```
cggggttaccc gggggccact taccgggatc ca                     32
```

<210> SEQ ID NO 54
<211> LENGTH: 38
<212> TYPE: DNA
<213> ORGANISM: Artificial Sequence
<220> FEATURE:
<223> OTHER INFORMATION: Probe for detection of ARMS amplification
      product of KRAS mutation Gln61Leu

<400> SEQUENCE: 54

```
cggggttaccc gggagtctcg gccacttacc gggatcca               38
```

<210> SEQ ID NO 55
<211> LENGTH: 241
<212> TYPE: DNA
<213> ORGANISM: Artificial Sequence
<220> FEATURE:
<223> OTHER INFORMATION: DNA fragment containing the positions that give
      rise to the 7 KRAS mutations Gly12Ser, Gly12Arg,
      Gly12Cys, Gly12Asp, Gly12Ala, Gly12Val & Gly13Asp

<400> SEQUENCE: 55

```
ggtggagtat ttgatagtgt attaacctta tgtgtgacat gttctaatat agtcacattt      60
tcattatttt tattataagg cctgctgaaa atgactgaat ataaacttgt ggtagttgga    120
gctggtggcg taggcaagag tgccttgacg atacagctaa ttcagaatca ttttgtggac    180
gaatatgatc caacaataga ggtaaatctt gttttaatat gcatattact ggtgcaggac    240
c                                                                    241
```